United States Patent [19]

Adams et al.

[11] Patent Number: 5,350,746
[45] Date of Patent: Sep. 27, 1994

[54] TRIAZOLYL AND TETRAZOLYL PHENYL SUBSTITUTED CARBAPENEMS, COMPOSITIONS CONTAINING SUCH COMPOUNDS AND METHODS OF USE

[75] Inventors: Alan D. Adams, Piscataway; James V. Heck, ScotchPlains, both of N.J.

[73] Assignee: Merck & Co., Inc., Rahway, N.J.

[21] Appl. No.: 48,534

[22] Filed: Apr. 14, 1993

[51] Int. Cl.$^5$ .............. A01K 43/00; A61K 31/395; C07D 487/00
[52] U.S. Cl. ........................ 514/210; 540/302
[58] Field of Search ............. 540/302; 514/210

[56] References Cited

U.S. PATENT DOCUMENTS

| | | |
|---|---|---|
| 4,260,627 | 4/1981 | Christensen et al. . |
| 4,269,772 | 5/1981 | Melillo et al. . |
| 4,309,438 | 1/1982 | Christensen et al. . |
| 4,350,631 | 9/1982 | Christensen et al. . |
| 4,383,946 | 5/1983 | Christensen et al. . |
| 4,414,155 | 11/1983 | Liu et al. . |
| 4,465,632 | 8/1984 | Christensen et al. . |
| 4,479,947 | 10/1984 | Christensen . |
| 4,543,257 | 9/1985 | Cama et al. . |
| 4,729,993 | 3/1988 | Christensen et al. . |
| 4,775,669 | 10/1988 | Cama et al. . |
| 4,962,101 | 10/1990 | Dininno et al. . |
| 4,978,659 | 12/1990 | Dininno et al. . |
| 5,004,739 | 4/1991 | Dininno et al. . |
| 5,004,740 | 4/1991 | Dininno et al. . |
| 5,006,519 | 4/1991 | Dininno et al. . |
| 5,011,832 | 4/1991 | Dininno et al. . |
| 5,025,006 | 6/1991 | Dininno et al. . |
| 5,025,007 | 6/1991 | Dininno et al. . |
| 5,025,008 | 6/1991 | Dininno et al. . |
| 5,032,587 | 7/1991 | Dininno et al. . |
| 5,034,384 | 7/1991 | Dininno et al. . |
| 5,034,385 | 7/1991 | Dininno et al. . |
| 5,037,820 | 8/1991 | Dininno et al. . |

FOREIGN PATENT DOCUMENTS 0277743 8/1988 European Pat. Off. .

OTHER PUBLICATIONS

Wentrup, C. et al. J. Am Chem. Soc. 102:6161–6163 (1980).
Melillo, D. G., et al. Tet. Let. 21:2783–2786 (1980).
De Vries, J. G., et al. Heterocycles 23(8):1915–1919 (1985).
Fuentes, L. M., et al., J. Am. Chem. Soc. 108: 4675–4676 (1986).
Cama, et al. Tetrahedron 39: 2531 (1983).
Guthikonda, et al. J. Med. Chem. 30: 871 (1987).
Bryce, et al. Bull. Soc. Chem. Fr. 1986 (6) 930–2.

*Primary Examiner*—Johann Richter
*Assistant Examiner*—Rebecca Cook
*Attorney, Agent, or Firm*—Richard C. Billups; Mark R. Daniel; Joseph F. DiPrima

[57] ABSTRACT

Triazolyl and tetrazolyl phenyl substituted carbapenems of the formula I are disclosed.

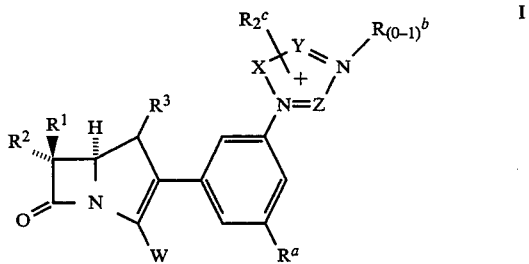

One or two of the variables X, Y and Z represent nitrogen atoms. The heteroaryl ting may be charged or uncharged.

Pharmaceutical compositions and methods of treatment are also disclosed.

11 Claims, No Drawings

TRIAZOLYL AND TETRAZOLYL PHENYL SUBSTITUTED CARBAPENEMS, COMPOSITIONS CONTAINING SUCH COMPOUNDS AND METHODS OF USE

BACKGROUND OF THE INVENTION

The present invention relates to antibacterial agents of the carbapenem class in which the five membered ring of the carbapenem nucleus is substituted with a triazolylphenyl or tetrazolylphenyl moiety at position 2.

Thienamycin was an early carbapenem antibacterial agent having a broad spectrum; it has the following formula:

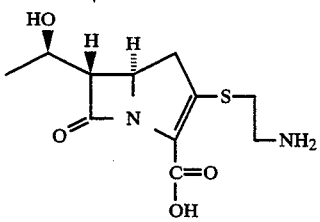

Later, N-formimidoyl thienamycin was discovered; it has the formula:

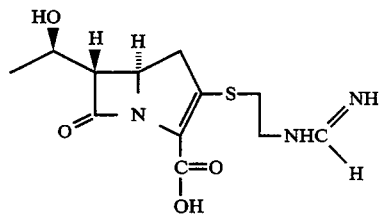

U.S. Pat. Nos. 5,011,832 and 5,025,006 relate to carbapenems of the structure shown below which exhibit antimicrobial activity against strains of methicillin resistant staphylococci (MRSA). The carbapenems described therein possess a meta-disposed biphenyl moiety attached to the C-2 position of the carbapenem ring.

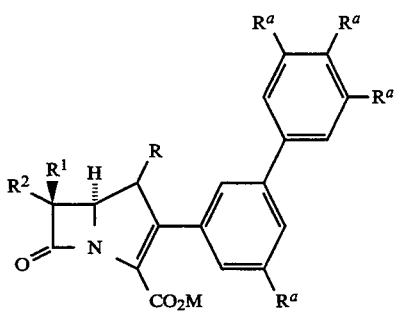

U.S. application Ser. No. 07/777,948 and U.S. application Ser. No. 07/957,974 relate to compounds wherein the substituent on the phenyl ring is an imidazolium or pyridinium group, each of which may be substituted. The heteroarylium group is typically attached to the phenyl ring through a heteroaryl ring nitrogen.

SUMMARY OF THE INVENTION

Triazolyl and tetrazolyl phenyl substituted carbapenems of the formula I are disclosed.

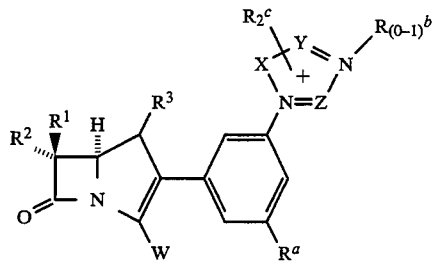

$R^1$ and $R^2$ independently represent H, $CH_3-$, $CH_3CH_2-$, $(CH_3)_2CH-$, $HOCH_2-$, $CH_3CH(OH)-$, $(CH_3)_2C(OH)-$, $FCH_2CH(OH)-$, $F_2CHCH(OH)-$, $F_3CCH(OH)-$, $CH_3CH(F)-$, $CH_3CF_2-$ or $(CH_3)_2CF-$.

$R^3$ is H or methyl.

$R^a$ is H or is selected from the group consisting of
a) $-CF_3$;
b) a halogen atom selected from the group consisting of: $-Br$, $-Cl$, $-F$ and $-I$;
c) a hydroxyl group
d) $-OC1-4$ alkyl, wherein the alkyl is optionally mono-substituted by Rq, where Rq is selected from the group consisting of $-OH$, $-OCH_3$, $-COOM$, with M representing H, a negative charge, a metal cation or an ester forming group, e.g., C1–4 alkyl;
e) $-NR'R''$ wherein R' and R'' independently represent H or C1–4 alkyl;
f) $-S(O)_n-R^s$, where n=0–2, and $R^s$ is C1–4 alkyl or phenyl, each of which is optionally mono-substituted by $R^q$ as defined above;
g) $-CN$;
h) a formyl or acetalized formyl radical which is $-C(O)H$ or $-CH(OCH_3)_2$;
i) $-C(O)R^s$, where $R^s$ is as defined above;
j) $-C(O)OC1-4$ alkyl, where the alkyl is optionally mono-substituted by $R^q$ as defined above;
k) $-C(O)N(R^y)R^z$, where $R^y$ and $R^z$ are independently H or C1–4 alkyl, (optionally mono-substituted by $R^q$ as defined above), or $N(R^y)R^z$ are taken together to represent an amino acid residue, or $R^y$ and $R^z$ are taken together to represent a 4- to 5-membered alkylidene radical which forms a ring (optionally substituted with $R^q$ as defined above), or a 3- to 4-membered alkylidene radical interrupted by $-O-$, $-S-$, $-S(O)-$ or $-S(O)_2-$ which forms a ring;
l) $-C(S)N(R^y)R^z$ where $R^y$ and $R^z$ are as defined above;
m) $-SCN$;
n) $-SCF_3$;
o) $-OCF_3$;
p) tetrazolyl, where the point of attachment is the carbon atom of the tetrazole ring and one of the nitrogen atoms is mono-substituted by hydrogen, an alkali metal or a C1–C4 alkyl;
q) a C2–C4 alkenyl radical, optionally mono-substituted by one of the substituents a) to p) above and phenyl which is optionally substituted by $R^q$ as defined above;
r) a C2–C4 alkynyl radical, optionally mono-substituted by one of the substituents a) to q) above;
s) a C1–C4 alkyl radical;

t) a C1–C4 alkyl group substituted with 1–3 groups $R^q$ as defined above, or mono-substituted by one of the substituents a)–s) above.

$R^b$ is present or absent. When $R^b$ is absent, the nitrogen which said group is shown optionally attached is uncharged. When $R^b$ is present, $R^b$ is selected from the group consisting of:

(a) —$C_{1-4}$ alkyl; (b) —NR'R" with R' and R" equal to H or $C_{1-4}$ alkyl and (c) $C_{1-4}$ alkyl substituted with up to three groups selected from:

hydroxy:
C1–4 alkoxy;
phenyl, nitrophenyl, methoxyphenyl or dimethoxyphenyl;
heteroaryl;
heteroaryl substituted with $R^s$, as defined above;
—NR'R", with R' and R" as defined above:
—OC(O)$R^s$, where $R^s$ is $C_{1-4}$ alkyl or phenyl, each of which is optionally mono-substituted by $R^q$ as defined above;
—C(O)—$R^s$ with $R^s$ as previously defined;
—C(O)N($R^y$)$R^z$, where $R^y$ and $R^z$ are as defined above;
—C(O)O$C_{1-4}$ alkyl, where the alkyl is optionally mono-substituted by $R^q$ as defined above; and
COOM, with M as defined above.

One or two of X, Y and Z represent a N atom and the other variables are carbon atoms.

Each $R^c$ is independently selected from the group consisting of hydrogen, halo, C1–4 alkyl; carboxyl: —COOM with M as previously defined, and C1–4 alkyl substituted with from 1 to 3 groups selected from:

hydroxy;
—C(O)—Rs with Rs as previously defined;
COOM, with M as previously defined;
—O—(C1–4) alkyl, wherein the alkyl portion is optionally substituted with Rq, as defined above;
—NR'R", with R' and R" as defined above;
—C(O)O(C1–4) alkyl, where the alkyl portion is optionally mono-substituted with Rq as defined above;
—C(O)N($R^y$)$R^z$, where $R^y$ and $R^z$ are independently H or C1–4 alkyl, (optionally mono-substituted by $R^q$ as defined above), or N($R^y$)$R^z$ are taken together to represent an amino acid residue, or $R^y$ and $R^z$ are taken together to represent a 4- to 5-membered alkylidene radical which forms a ring (optionally substituted with $R^q$ as defined above), or a 3- to 4-membered alkylidene radical interrupted by —O—, —S—, —S(O)— or —S(O)$_2$— which forms a ring; and
—OC(O)N($R^y$)$R^z$, where $R^y$ and $R^z$ are as defined independently or in combination with the N to which they are attached.

Alternatively, the two Rc groups may be taken in combination to represent an aromatic ting fused to the triazolyl or tetrazolyl ting to which they are attached, said aromatic 5–6 membered ring selected from the group consisting of phenyl, pyridine, pyrazine, pyrimidine, pyrrole, imidazole, thiophene, furan and thiazole.

W is selected from: —COOH, or a pharmaceutically acceptable salt or ester thereof; COORP where RP is a readily removable carboxyl coveting group which is not a pharmaceutically acceptable ester; COOM$^a$ where M$^a$ is an alkali metal, or a negative charge.

DETAILED DESCRIPTION OF THE INVENTION

The invention is described herein in detail using the terms defined below unless otherwise specified.

The term "alkyl" refers to a monovalent alkane (hydrocarbon) derived radical containing from 1 to 10 carbon atoms unless otherwise defined. It may be straight, branched or cyclic. Preferred alkyl groups include methyl, ethyl, propyl, isopropyl, butyl, t-butyl, cyclopentyl and cyclohexyl. When substituted, alkyl groups may be substituted with up to three substituent groups, at any available point of attachment. When the alkyl group is said to be substituted with an alkyl group, this is used interchangeably with "branched alkyl group".

Cycloalkyl is a specie of alkyl containing from 3 to 15 carbon atoms, without alternating or resonating double bonds between carbon atoms. It may contain from 1 to 4 rings which are fused.

The term "alkenyl" refers to a hydrocarbon radical straight, branched or cyclic containing from 2 to 10 carbon atoms and at least one carbon to carbon double bond. Preferred alkenyl groups include ethenyl, propenyl, butenyl and cyclohexenyl.

The term "alkynyl" refers to a hydrocarbon radical straight, branched or cyclic, containing from 2 to 10 carbon atoms and at least one carbon to carbon triple bond. Preferred alkynyl groups include ethynyl, propynyl and butynyl.

Aryl refers to aromatic rings e.g., phenyl, substituted phenyl and the like, groups as well as rings which are fused, e.g., naphthyl, phenanthrenyl and the like. Aryl thus contain at least one ring having at least 6 atoms, with up to five such rings being present, containing up to 22 atoms therein, with alternating (resonating) double bonds between adjacent carbon atoms or suitable heteroatoms. The preferred aryl groups are phenyl, naphthyl and phenanthrenyl. Aryl groups may likewise be substituted as defined below. Preferred substituted aryls include phenyl substituted with one or two groups.

The term "heteroaryl" refers to a monocyclic aromatic hydrocarbon group having 5 or 6 ring atoms, or a bicyclic aromatic group having 8 to 10 atoms, containing at least one heteroatom, O, S or N, in which a carbon or nitrogen atom is the point of attachment, and in which one additional carbon atom is optionally replaced by a heteroatom selected from O or S, and in which from 1 to 3 additional carbon atoms are optionally replaced by nitrogen heteroatoms, said heteroaryl group being optionally substituted with up to four $R^q$ groups.

Heteroaryl thus includes aromatic and partially aromatic groups which contain one or more heteroatoms. The monocyclic heteroaryl has at least one nitrogen atom, and optionally one additional oxygen or sulfur heteroatom may be present. Examples of this type are pyrrole, pyridine, oxazole, thiazole and oxazine. Additional nitrogen atoms may be present together with the first nitrogen and oxygen or sulfur, giving, e.g., thiadiazole. The preferred heteroaryls are those where only nitrogen heteroatoms are present when there is more than one. Typical of these are pyrazole, tetrazole, imidazole, pyrimidine and pyrazine and triazine.

When the term "aromatic" is used to describe a ring fused to the triazole or tetrazole ring, such as when the two Rc groups are considered in combination, this aromatic ting can be an aryl or heteroaryl ring. Fusion typically is through carbon atoms, but may also include nitrogen atoms in certain instances.

The term "heterocycloalkyl" refers to a cycloalkyl group (nonaromatic) in which one of the carbon atoms in the ring is replaced by a heteroatom selected from O, S, NH, or N(C1–C4 alkyl), and in which up to three additional carbon atoms may be replaced by said hetero groups.

The term "quaternary nitrogen" refers to a tetravalent positively charged nitrogen atom including, e.g., the positively charged nitrogen in a tetraalkylammonium group (e.g. tetramethylammonium, N-methylpyridinium), the positively charged nitrogen in a protonated ammonium species (e.g. trimethylhydroammonium, N-hydropyridinium), the positively charged nitrogen in an amine N-oxide (e.g. N-methylmorpholine-N-oxide, pyridine-N-oxide), and the positively charged nitrogen in an N-amino-ammonium group (e.g. N-aminopyridinium).

The term "heteroatom" means N, S, or O, selected on an independent basis.

Alkylene (alkylidene or alkanediyl) and arylene refer to the groups noted above with divalent points of attachment. For example, phenylene is an arylene group, attached at any of the 1, 2- 1, 3- or 1, 4-positions. Examples of alkylene include —CH$_2$—, —CH$_2$CH$_2$—, —CH$_2$CH$_2$CH$_2$—,

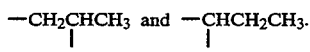

Similarly, alkanetriyl refers to an alkane-derived group with three points of attachment. Alkanetriyl groups from five to fifteen carbon atoms, which may be straight, branched, cyclic or multicyclic.

Aralkyl is a specie of substituted alkyl, containing up to three aryl groups substituted on a straight, branched or cycloalkyl group. The most preferred aralkyl group is benzyl.

Halogen, or "halo" refers to atoms of bromine, chlorine, fluorine and iodine.

Alkoxy refers to C$_1$–C$_4$ alkyl—O—, with the alkyl group optionally substituted with the variable R$^q$.

Carbonyloxy refers to the radical: —OC(O)R$^s$, where R$^s$ is C$_{1-4}$ alkyl or phenyl, each of which is optionally mono substituted by R$^q$.

Carbamoyloxy refers to the radical: —OC(O)N-(R$^y$)R$^z$, where R$^y$ and R$^z$ are independently H, C$_{1-4}$ alkyl, (optionally mono-substituted by R$^q$ as defined above). Alternatively, R$^y$ and R$^z$ can be taken in combination with the nitrogen to which they are attached to represent an amino acid residue, or taken together to represent a 4- to 5-membered alkylidene radical which forms a ring (optionally substituted with R$^q$ as defined above), or a 3- to 4-membered alkylidene radical interrupted by —O—, —S—, —S(O)— or —S(O)$_2$— which forms a ring, said ring being optionally mono-substituted with R$^q$ as defined above.

A "carbonyl radical" is represented by the formula: —C(O)R$^s$, where R$^s$ is as defined above.

An "alkoxycarbonyl" radical is represented by the formula: —C(O)OC$_{1-4}$ alkyl, where the alkyl is optionally mono-substituted by R$^q$ as defined above.

A "carbamoyl" radical is represented by the formula: —C(O)N(R$^y$)R$^z$, where R$^y$ and R$^z$ are as defined independently or in combination with the nitrogen to which they are attached.

When N(R$^y$)R$^z$ is taken to represent an amino acid residue, one of R$^y$ and R$^z$ represents H and the other represents the amino acid alkyl group in most instances. When the group represents a proline residue, N, R$^y$ and R$^z$ are taken together to represent the group:

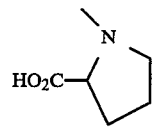

An "N-hydroxycarbamoyl or N(C$_1$–C$_4$ alkoxy)carbamoyl" radical in which the nitrogen atom may be additionally substituted by a hydroxyl or C$_1$–C$_4$ alkyl group.

A "carboxyl group" is represented by the structural formula: —COOM where M is as defined above.

The compounds of the present invention are substituted at position 2 of the carbapenem nucleus with a phenyl ring. The phenyl ring bears a triazole or tetrazole substituent at position 3′, and optionally bears a substituent R$^a$ at position 5′. One of the triazole and tetrazole ting nitrogens may be quaternized by virtue of the R$^b$ group attached thereto. Thus, the triazolyl group may also be referred to as a triazolium ring, and the tetrazole group may also be referred to as a tetrazolium ring. For the triazoles, the compounds are preferably positively charged in the triazolium ring and negatively charged at the carboxylate on position three of the carbapenem nucleus. For the tetrazoles, the tetrazole ring is less stable when in the charged form, so the preferred tetrazoles are uncharged.

The preferred value of R$^1$ is hydrogen. The preferred values of R$^2$ are (R) CH$_3$CH(OH)— and (R) CH$_3$CH(F)—. The most preferred value of R$^2$ is (R) CH$_3$CH(OH)—.

The preferred value of R$^3$ is methyl, and most preferably a beta methyl group.

The preferred values of W are —COO—, —COOM, with M representing an alkali metal cation and —COOR$^p$ with R$^p$ representing a protecting group.

The preferred values of R$^a$ include H, halo groups, e.g., I, Br and Cl, —CF$_3$, —SCH$_3$ and methoxy.

When a group is termed "substituted", unless otherwise indicated, this means that the group contains from 1 to 3 substituents R$^q$ thereon.

Preferred substituent groups include C$_{1-4}$ alkyl and hydroxy.

When a functional group is termed "protected", the group is in modified form to preclude undesired side reactions at the protected site. Suitable protecting groups for the compounds of the present invention will be recognized from the present application taking into account the level of skill in the art, and with reference to standard textbooks, such as McOmie, J. (Ed) Protecting Groups in Organic Chemistry pp. 46–119 (1973).

The novel carbapenem compounds can be protected in the form —COOR$^p$, where R$^p$ in many instances is a readily removable carboxyl protecting group. Such conventional groups consist of known groups which are used to protectively block the carboxyl group during the synthesis procedures described therein. These conventional blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile and catalytic hydrogenation.

Examples of such ester protecting groups include benzhydryl, p-nitrobenzyl, 2-naphthylmethyl, allyl, benzyl, trichloroethyl, silyl such as trimethylsilyl or trimethylsilylethyl, phenacyl, p-methoxybenzyl, acetonyl, o-nitrobenzyl, p-methoxyphenyl, 4-pyridylmethyl, and t-butyl. Other suitable protecting groups for the carboxylate at position three include 2-chloroallyl, t-butyldimethylsilyl, t-butyldiphenylsilyl, 2-(trimethylsilyl)ethyl, phenacyl, 4-pyridylmethyl and t-butyl.

The preferred protecting groups for the carboxylate group at position three of the carbapenem nucleus are p-nitrobenzyl, methoxybenzyl, dimethoxybenzyl and diphenylmethyl groups.

When one of $R^1$ and $R^2$ bears a hydroxyl group, and when any of the other variables, e.g., $R^q$ includes a hydroxyl group, it may be necessary to protect these groups during the synthesis. The preferred protecting groups for hydroxyl groups include various silyl compounds, e.g., t-butylmethoxyphenylsilyl, t-butoxydiphenylsilyl, trimethylsilyl and t-butyldimethylsilyl groups. Other suitable protecting groups include o-nitrobenzyloxycarbonyl, p-nitrobenzyloxycarbonyl, benzyloxycarbonyl, t-butyloxycarbonyl, 2,2,2-trichloroethyloxycarbonyl and allyloxycarbonyl.

The term "metal cation" refers to cations which are biologically compatible, e.g., Na, K, Mg and the like, as well as metals which are useful during the synthesis of the molecule of interest. If the metal cation used during the synthesis is not desirable in the final dosage formulation, it can be replaced with a biocompatible metal cation prior to formulation or administration to the patient.

The compounds of the invention can be positively charged in the triazolium or tetrazolium ting, negatively charged by virtue of the carboxylic acid (carboxylate) group attached to the carbapenem nucleus, or by virtue of a substituent group attached to the phenyl or triazolyl/tetrazolyl group, or may have a net electrical charge of zero: the compounds may be zwitterionic.

The preferred compounds of the invention are positively charged or are zwitterionic. The positively charged compounds are preferably found in combination with a biocompatible, negatively charged specie, shown in the syntheses below as delta (minus). These may include biocompatible anions, e.g., Cl—, phosphates and sulfate anions which are partially protonated and the like. The charged compounds of the invention will typically be found in the presence of a suitable counterion.

Synthesis of the target compounds generally consists of the attachment of a completely or partially elaborated aryl sidechain onto a protected bicyclic azetidinone. For purposes of description, the synthesis is divided into the synthesis of the aryl sidechain coupling partner, the coupling of that sidechain to the bicyclic azetidinone and the deprotection of the resulting 2-aryl carbapenem. The key intermediate in the syntheses is the 3′,5′-disubstituted aryl triazolium stannane C3, or the tetrazole or tetrazolium analogs E3, E4 or E5, or F4 or F5. Representative routes to these intermediates are outlined in schemes I, II, V and VI.

The synthesis of the substituted meta (trimethylstannyl)phenyltriazoles shown below can be approached by several routes. Introduction of the intact triazolium ring, by displacement, into an aryl ring can be used when the aryl halide substrate is readily available. Displacement of halides, particularly fluoride have proven to be broadly applicable. Alteratively, the ring may be constructed from readily available anilines by any of several routes for the various triazolium analogs.

Examples are provided below of the construction of substituted N-aryl 1,2,4- and 1,2,3-triazoles by displacement of fluorobenzene derivatives, and alternative constructions by synthesis of the 1,2,3- and 1,2,4-triazole ring by ring synthesis, ultimately deriving from readily available anilines, and hydrazines as in scheme II.

The 1-[3′-(trimethylstannyl)-5′-chlorophenyl](1,2,4)-triazole is readily prepared by the condensation of the sodium derivative of 1,2,4-triazole and commercially available bromochlorofluorobenzene in N-methylpyrrolidinone (NMP) at 90° to 120° C. for ½ to 24 Hrs. The products from these condensations are typically obtained in 40–80% yield. The reaction is applied to the 1,2,3- and 1,2,4-triazoles with equal efficacy.

The 1-[3′-bromo-5′-chlorophenyl](1,2,4)triazole is convened to the desired stannane derivative by catalytic stannylation with $(Me_3Sn)_2$ and palladium tetrakistriphenylphosphine [$(Ph_3P)_4Pd$]. Typical yields are 80–85%.

In general, fluorobenzene substrates substituted with $R^a$ are obtained by the well known thermolysis of the aryl diazonium tetrafluoroborate salt (the Schiemann reaction). The anilines used also derive from the anilines shown in scheme II. Application of routine protection and deprotection chemistry, and simple functional group transformations allows access to a broad variety of analogs. Convenience and functional group comparability will decide the favored route in each case.

The triazolium stannanes are alkylated with alkyl or benzyl trifluoromethanesulfonates, bromides, iodides or other alkylating agents to yield the key synthetic intermediate C9 in Scheme III.

Scheme I

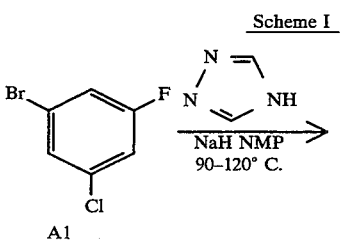

A1

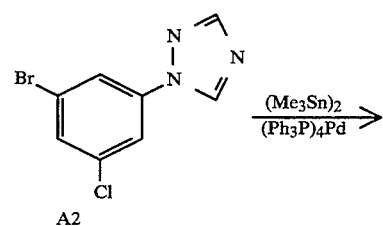

A2

-continued
Scheme I

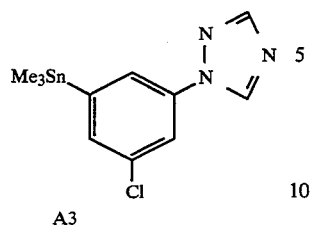
A3

General Synthesis of A1

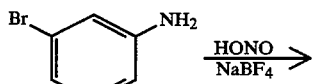
A4
See Scheme II for A4

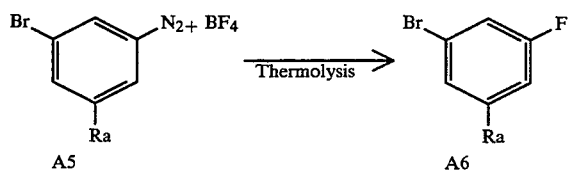
A5    A6

General Conversion to A9:

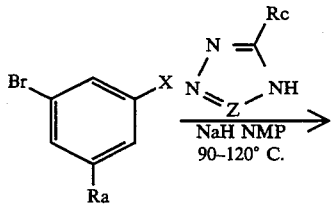
A7
X = Leaving group
    Preferably F, also Br, OTf.

-continued
Scheme I

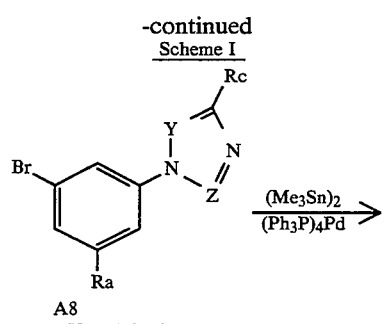
A8
Y or Z is nitrogen

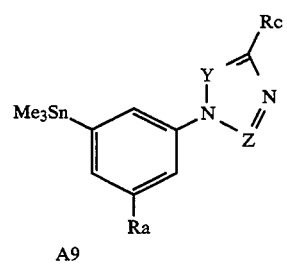
A9

Alternate routes are sketched out for typical ring formation strategies in Scheme II. The syntheses originate with readily available $R^a$ substituted nitro anilines. The bromo substituent is introduced, and the nitro aniline B2 convened to the desired 1,3,5-trisubstituted aniline A4 by well known reduction-oxidation sequences. The 1,2,4-triazole B6 is readily prepared from the substituted phenylhydrazines shown by condensation with the iminium salt B5 shown (See Gold, H. Angew. Chem. 72(24),956, 1960, and references therein). The condensation typically gives good to moderate yields of product.

An alternate route to the 1,2,3-triazole B9 is depicted in the same scheme from a substituted phenyl azide B7. Cyclocondensation with butyl vinylether, followed by dehydration leads again to good to moderate yields of the desired triazole B9 (See Huisgen, R.; Mobius, L.; Sziemies, G Chem. Ber. 98, 1138-1152, 1965, and references therein.). Several other possible routes are well known for the construction of a triazole ring from an aryl amine derivative.

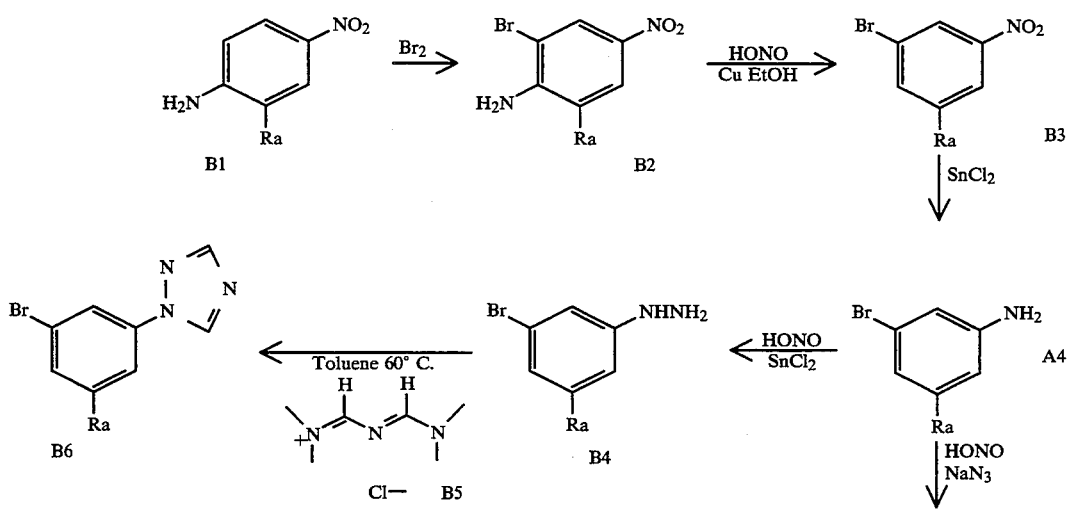

-continued
Scheme II

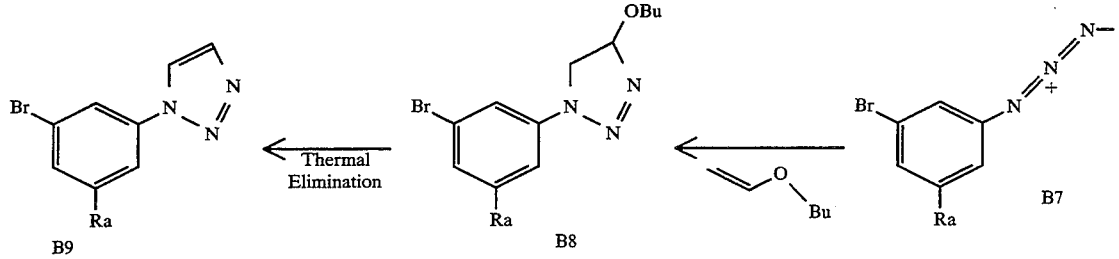

The completely elaborated sidechain is coupled to the bicyclic azetidinone as shown in Scheme III, by a variation of a previously reported reaction. Usual reaction conditions involve the conversion of the bicyclic azetidinone β-ketoester C1 to the enol trifluoromethanesulfonate (triflate) C2 in situ, followed by the palladium catalyzed coupling of the sidechain.

The formation of the enol triflate is typically performed in $CH_2Cl_2$ or other inert solvent at $-78°$ C. A slight excess of a tertiary amine base, typically diisopropylethyl amine, is added, followed by brief stirring, and the addition of a similar excess of trifluoromethanesulfonic anhydride (triflic anhydride). The conversion to the enol triflate is usually complete in less than twenty minutes. The coupling of the aryl sidechain is achieved by the addition of a palladium catalyst, and the aryl stannane. Typically a promoter is required to accelerate the coupling reaction. In the present cases either one equivalent or less of tetraalkylammonium chloride, or an equal volume of NMP is used as promoter. The best catalyst for the coupling reaction depends to some degree on the aryl stannane substrate. In general, palladium acetate is used; in some cases $Pd_2(DBA)_3$—$CHCl_3$ is preferable. Coupling reactions are generally complete in less than two hours. When charged products are obtained, the products are purified without workup by chromatography on an RP-18 adsorbent.

The deprotection of the ester products to the desired carbapenem carboxylate is achieved by hydrogenation of the p-nitrobenzyl (PNB) esters in THF/water or $THF/H_2O$/ethanol with 10–15% (weight) 5% Rh on $Al_2O_3$. An excess of sodium bicarbonate is added to the reaction mixture to generate the desired sodium salt or zwitterionic product. The reaction mixtures are also chromatographed on an RP-18 adsorbent directly after filtration and removal of the organic solvent i. vac.

Scheme IV

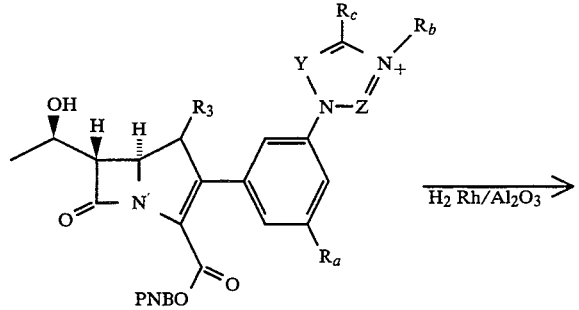

Scheme III

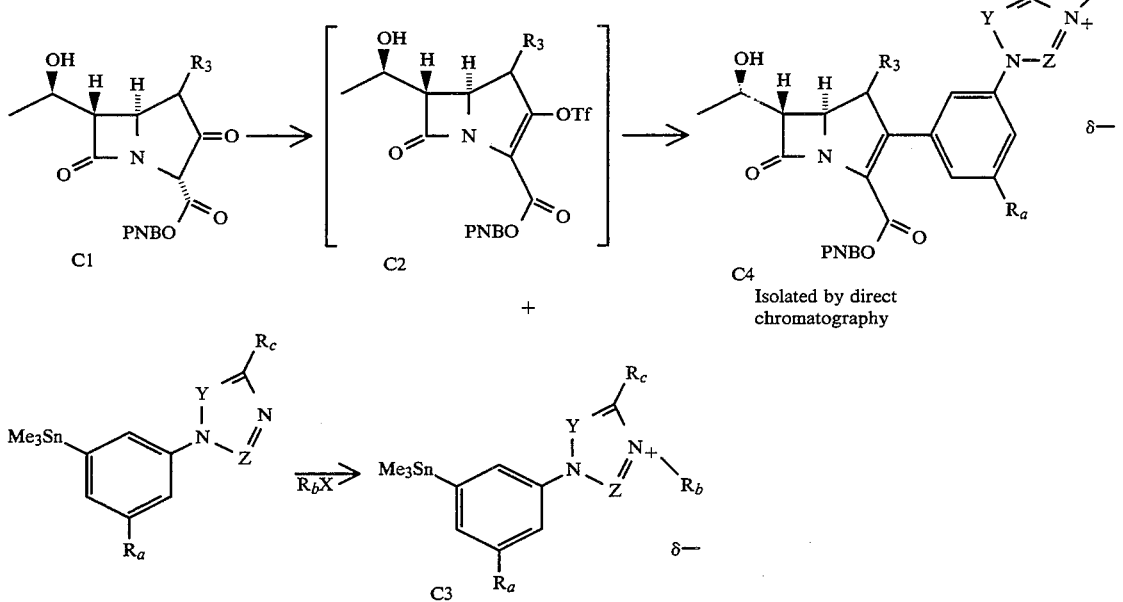

-continued
Scheme IV

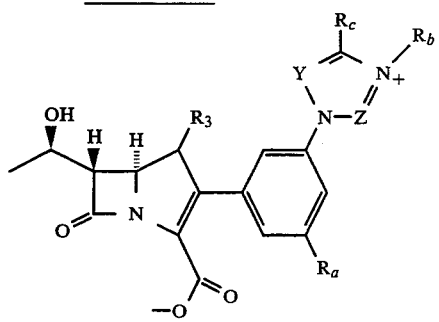

shown in schemes V and VI below. Again beginning with the aniline A4, the 1-aryl tetrazole analogs are prepared by the well known annulation shown in scheme V, (See Hagedorn, I.;Winkelmann H.-D. Chem. Ber. 99, 850–855, 1966. and refernces therein.) and converted to the stannane intermediate E3 under conditions similar to those used for the triazoles above. Either the uncharged stannane E3, or the alkylated stannane E4 or E5 is coupled to the bicyclic azetidinone C1 as shown for the triazolium analogs in scheme III. The deprotection of the ester intermediates differs little from the corresponding triazolium analog, as shown in scheme IV.

Scheme V

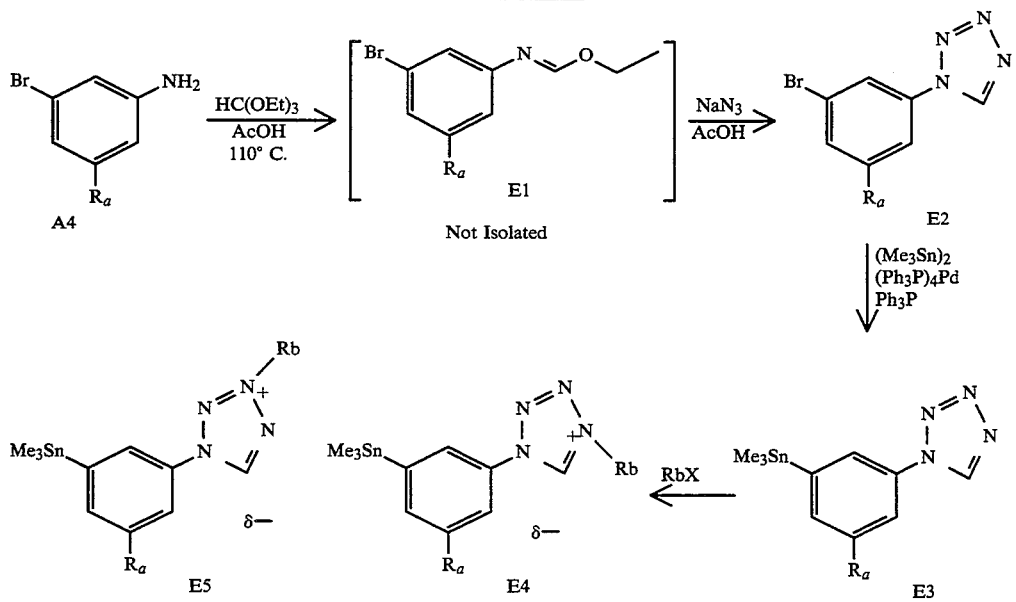

General synthesis of 1-Aryl tetrazoles

Synthesis of the analogous tetrazole analogs uses a similar strategy with the similar key intermediates The 2-aryl tetrazole intermediates are prepared by a different annulation, shown in scheme VI, starting with the hydrazine derivatives B4 found in scheme II.

Scheme VI

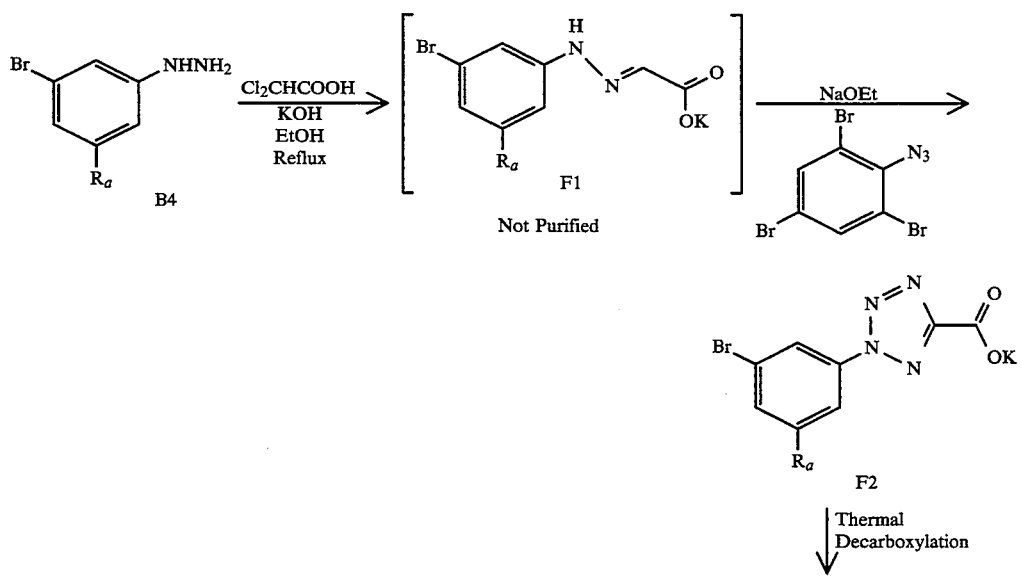

-continued
Scheme VI

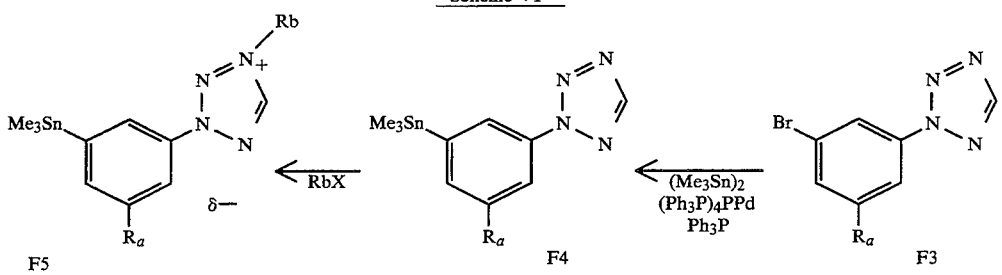

General synthesis of 2-Aryl tetrazoles

The tetrazolylaryl derivatives are converted to the stannane, and alkylated as for the similar triazolylaryl derivatives above. The coupling and deprotection reactions are again performed as for the triazolium analogs in scheme III and IV.

In the compounds of the present invention, the $R^a$ substituent may contribute to the anti-MRSA/MRCNS activity of the overall molecule, or to the other properties of the molecule.

Some $R^a$ substituents may be distinguishable from others chemically or with respect to the biological properties which they confer. In related compounds, it has been found that the charged compounds may afford greater water solubility. Substituents which tend to confer improved water solubility on the overall compound have been found useful, since they are contemplated to improve the pharmacokinetics of the compound involved. Although a substantial number and range of $R^a$ substituents has been described herein, all of these are contemplated to be a part of the present invention in connection with the genus of formula I.

The carbapenem compounds of the present invention are useful per se and in their pharmaceutically acceptable salt and ester forms for the treatment of bacterial infections in animal and human subjects. The term "pharmaceutically acceptable ester, salt or hydrate," refers to those salts, esters and hydrated forms of the compounds of the present invention which would be apparent to the pharmaceutical chemist from the teachings herein. i.e., those which are substantially non-toxic and which may favorably affect the pharmacokinetic properties of said compounds, their palatability, absorption, distribution, metabolism and excretion. Other factors, more practical in nature, which are also important in the selection, are cost of the raw materials, ease of crystallization, yield, stability, hygroscopicity, and flowability of the resulting bulk drag. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel carbapenem compounds.

The pharmaceutically acceptable salts referred to above may take the form —COOM$^a$. The M$^a$ may be a negative charge, or an alkali metal cation such as sodium or potassium. Other pharmaceutically acceptable cations may be calcium, magnesium, zinc, ammonium, or alkylammonium cations such as tetramethylammonium, tetrabutylammonium, choline, triethylhydroammonium, meglumine, triethanolhydroammonium, etc.

The Formula I compounds can be used in the form of salts derived from inorganic or organic acids. Included among such salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate. tartrate, thiocyanate, tosylate, and undecanoate.

The pharmaceutically acceptable esters of the present invention include, for example, those described in detail in U.S. Pat. No. 4,309,438. Included within such pharmaceutically acceptable esters are those which are hydrolyzed under physiological conditions, such as pivaloyloxymethyl, acetoxymethyl, phthalidyl, indanyl and methoxymethyl, and others described in detail in U.S. Pat. No. 4,479,947.

The esters which are hydrolizable under physiological conditions are also referred to as "biolabile esters". Many biolabile esters have oral activity, protecting the drug from excessive acid degradation upon oral administration. Biolabile esters are biologically hydrolizable, and many are suitable for oral administration, due to good absorption through the stomach or intestinal mucosa, resistance to gastric acid degradation and other factors. The following M species are preferred as biolabile ester foraging moieties.: acetoxymethyl, 1-acetoxyethyl, 1-acetoxypropyl, pivaloyloxymethyl, 1-isopropyloxycarbonyloxyethyl, 1-cyclohexyloxycarbonyloxyethyl, phthalidyl and (2-oxo-5-methyl-1,3-dioxolen-4-yl)methyl.

The compounds of the present invention are active against various Gram-positive and Gram-negative bacteria, and accordingly find utility in human and veterinary medicine. The antibacterials of the invention are not limited to utility as medicaments; they may be used m all manner of industry, for example: additives to animal feed, preservation of food, disinfectants, and in other industrial systems where control of bacterial growth is desired. For example, they may be employed in compositions in concentrations ranging from about 0.01 to about 100 parts of antibiotic per million parts of solution in order to destroy or inhibit the growth of harmful bacteria on medical and dental equipment and as bactericides in industrial applications, for example in water based paints and in the white water of paper mills to inhibit the growth of harmful bacteria.

Many of compounds of the present invention are biologically active against MRSA/MRCNS. This can be demonstrated using the following biological activity protocol.

In vitro antibacterial activity determined in accordance with the protocol set forth below is predictive of in vivo activity, when the compounds are administered to a mammal infected with a susceptible bacterial organism.

Minimum inhibitory concentrations for different compounds may be calculated using the procedures set forth in Lorian, V. (ed.) *Antibiotics in Laboratory Medicine* (3rd ed.) pages 30–35 if desired. However, by comparing disc sensitivities to a known compound, e.g., imipenem, this calculation is not required to recognize MRSA/MRCNS activity.

Assay Used to Test the Activities of Carbapenems Against Methicillin-Resistant Staphylococci The assay is an antibiotic disc-diffusion assay modeled after the method described by Bauer and Kirby, et al., with the following modifications and clarifications:

Agar: This assay employs an agar depth of 2 mm instead of 4 mm. Zone Readings: The inner, completely clear zone is measured.

Culture Storage: Frozen vials of strains are stored at −80° C. Working slants are prepared from frozen vials and are used for 1 month to 6 weeks. For methicillin-resistant strains the slant medium is Mueller Hinton Agar; for control strains the slant medium is Brain Heart Infusion Agar. After inoculation from frozen vials, methicillin-resistant slant cultures are incubated at 28° C. until good growth is achieved (approximately 20 hours); slants of control strains are incubated at 37° C. for 16–18 hours.

Preparation of Control Inocula for Assay: Pipette 2 ml Brain Heart Infusion Broth (BHIB) into a sterile, plastic 17×100 mm tube. Use a sterile cotton tipped applicator to pick up a very small amount of culture from the slant and twirl it in the BHIB to achieve a light but visible inoculum (approximately $1 \times 10^6 - 10^7$ cuf/ml). Incubate at 37° C. and 220 rpm for 17–18 hours.

Preparation of Methicillin-Resistant Inocula for Assay: For methicillin-resistant strains, inoculate 0.5 ml of BHIB heavily (to achieve approximately $1 \times 10^8 - 10^9$ cfu/ml) from the slant culture by using a sterile cotton tipped applicator. With the applicator spread approximately 0.1 ml of the suspension onto the surface of a 15×100 mm petri plate containing 10 ml Mueller Hinton Agar. Incubate the plate at 30° C. for approximately 18 hours.

Inoculum Adjustment: The 17–18 hour control Staphylococci cultures are diluted 100× in phosphate-buffered saline (PBS).

Methicillin-resistant Staphylococci: With a cotton tipped applicator, swab enough growth off the grown plates into 1 ml BHIB to achieve a visual concentration of approximately $1 \times 10^9$ cfu/ml. Mix vigorously and dilute in PBS so that dilutions appear visually to be slightly more concentrated than the 100× diluted control cultures. Measure % transmission (%T) at 660 nm in a Spectronic 20 or other spectrophotometer. Add measured quantities of PBS to dilutions to achieve %T@1% above or below the %T measurement for the control cultures. Make sterile dilutions using the same proportions.

Plate Incubation Following Plate Inoculation and Disc Placement: Incubate control plates for 18 hours at 37° C. Incubate methicillin-resistant Staphylococci plates for 18 hours at 30° C.

The compounds of this invention may be used in a variety of pharmaceutical preparations. They may be employed in powder or crystalline form, in liquid solution, or in suspension. They may be administered by a variety of means; those of principal interest include: topically, orally and parenterally by injection (intravenously or intramuscularly).

Compositions for injection, a preferred route of delivery, may be prepared in unit dosage form in ampoules, or in multidose containers. The injectable compositions may take such forms as suspensions, solutions, or emulsions in oily or aqueous vehicles, and may contain formulating agents. Alternatively, the active ingredient may be in powder (lyophilized or non-lyophilized) form for reconstitution at the time of delivery with a suitable vehicle, such as sterile water.

Topical applications may be formulated in hydrophobic or hydrophilic bases as ointments, creams, lotions, paints or powders.

Oral compositions may take such forms as tablets, capsules, oral suspensions and oral solutions. The oral compositions may utilize conventional formulating agents, and may include sustained release properties as well as rapid delivery forms.

The dosage to be administered depends to a large extent upon the condition and size of the subject being treated, the route and frequency of administration, the sensitivity of the pathogen to the particular compound selected, the virulence of the infection and other factors. Such matters, however, are left to the routine discretion of the physician according to principles of treatment well known in the antibacterial arts. Another factor influencing the precise dosage regimen, apart from the nature of the infection and peculiar identity of the individual being treated, is the molecular weight of the compound.

The compositions for human delivery per unit dosage, whether liquid or solid, may contain from about 0.01% to as high as about 99% of active material, the preferred range being from about 10–60%. The composition will generally contain from about 15 mg to about 2.5 g of the active ingredient; however, in general, it is preferable to employ a dosage amount in the range of from about 250 mg to 1000 mg. In parenteral administration, the unit dosage will typically include the pure compound in sterile water solution or in the form of a soluble powder intended for solution, which can be adjusted to neutral pH and isotonicity.

The preferred methods of administration of the Formula I antibacterial compounds include oral and parenteral, e.g., i.v. infusion, i.v. bolus and i.m. injection.

For adults, about 5–50 mg of Formula I antibacterial compound per kg of body weight given one to four times daily is preferred. The preferred dosage is 250 mg to 1000 mg of the antibacterial given one to four times per day. More specifically, for mild infections a dose of about 250 mg two or three times daily is recommended. For moderate infections against highly susceptible gram positive organisms a dose of about 500 mg three or four times daily is recommended. For severe, life-threatening infections against organisms at the upper limits of sensitivity to the antibiotic, a dose of about 1000–2000 mg three to six times daily may be recommended.

For children, a dose of about 5–25 mg/kg of body weight given 2, 3 or 4 times per day is preferred; a dose of 10 mg/kg is typically recommended.

The compounds of Formula I are of the broad class known as carbapenems. Some carbapenems are susceptible to attack by a renal enzyme known as dehydropeptidase (DHP). This attack or degradation may reduce the efficacy of the carbapenem antibacterial agent. The compounds of the present invention, on the other hand, are less subject to such attack, and therefore may not require the use of a DHP inhibitor. Such use is therefore optional and contemplated to be part of the present invention. Inhibitors of DHP and their use with carbapenems are disclosed in, e.g., [European Patent Application Nos. 79102616.4, filed Jul. 24, 1979 (U.S. Pat. No. 0,007,614); and 82107174.3, filed Aug. 9, 1982 (Publication No. 0 072 014)].

The compounds of the present invention may, where DHP inhibition is desired or necessary, be combined or used with the appropriate DHP inhibitor as described in the aforesaid patents and published application. The cited European Patent Applications define the procedure for determining DHP susceptibility of the present carbapenems and disclose suitable inhibitors, combination compositions and methods of treatment. A preferred weight ratio of Formula I compound: DHP inhibitor in the combination compositions is about 1:1.

A preferred DHP inhibitor is 7-(L-2-amino-2-carboxyethylthio)-2-(2,2-dimethylcyclopropanecarboxamide)-2-heptenoic acid or a useful salt thereof.

The invention is further described in connection with the following non-limiting examples.

EXAMPLE ONE

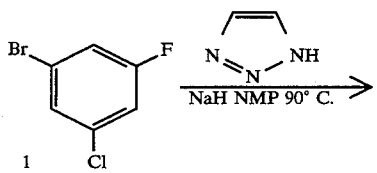

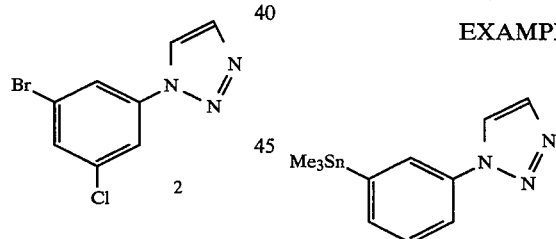

Sodium hydride (1.1 Eq, 0.021 mol, 840 mg, 60% dispersion in oil) was washed three times with hexanes, and dried under a stream of nitrogen. NMP (10 ml) was added, followed by dropwise addition of (1,2,3)-triazole (1.0 Eq, 0.019 mol, 1.1 ml, 1.32 g). The rate of addition was adjusted to give a manageable gas evolution. The mixture was stirred briefly to give a homogenous solution. Neat 1,3,5-bromochlorofluorobenzene (1.0 Eq, 0.019 mol, 2.3 ml, 4 g) was added, and the mixture heated to 90° C. for 15 Hrs. The reaction mixture is poured into water (300 ml), stirred briefly and filtered. The solid residue was washed with water and air dried. The crude material was purified by chromatography on SiO2 (200 g) eluting with toluene: ethyl acetate 96:4. The desired product 2 was obtained as colorless crystals (2.1 g) in 43% yield.

$^1$H NMR 400 MHz (CDCl$_3$) 7.57 (t, 1H, J=1.8 Hz), 7.74 (t, 1H, J=1.9 Hz), 7.84 (t, 1H, J=1.8 Hz), 7.85 (d, 1H, J=1.2 Hz), 7.97 (d, 1H, J=1.2 Hz).

EXAMPLE TWO

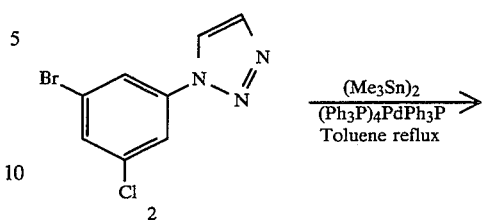

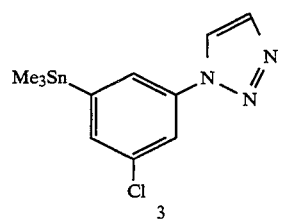

The Bromide 2 ( 1.0 Eq, 7.9 mmol, 2 g) was dissolved in toluene (60 ml) with (Me$_3$Sn)$_2$ (1.2 Eq, 9.5 mmol, 2.0 ml), triphenylphosphine (0.05 Eq, 0.4 mmol, 104 mg) and (Ph$_3$P)$_4$Pd (0.05 Eq, 0.4 mmol, 450 mg). The reaction vessel was flushed by vacuum versus nitrogen purge, and the mixture heated to reflux. The reaction is complete at ~1 Hr. The solution was cooled and diluted with ethyl acetate. The organic fraction was washed twice with dil. Na$_2$CO$_3$, once with brine, and dried over Na$_2$SO$_4$. The solution was reduced i. vac and chromatographed on SiO$_2$ (80 g) eluting with 15% ethyl acetate in hexanes. The desired product 3 is obtained as colorless crystals, 2.71 g, 75%.

$^1$H NMR 400 MHz (d-6 Acetone) 8.65 (d, 1H, J=1.1 Hz), 7.99 (m, 1H), 7.88 (m, 2H), 7.61 (m, 1H), 0.39 (m, 9H, J=27.5 Hz), Note: 7.61 and 7.99 ppm multiplets are doublets J=1.5 Hz, with additional coupling to Sn.

EXAMPLE THREE

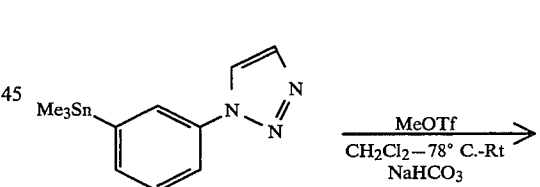

The Stannane 3 (1.0 Eq, 2.9 mmol, 1.0 g) was dissolved in distilled CH$_2$Cl$_2$ (5 ml), with NaHCO$_3$ (1.5 Eq, 4.4 mmol, 370 mg). The suspension was cooled to −78° C., and methyl triflate (1.5 Eq, 4.4 mmol, 0.5 ml) was added. The mixture was allowed to come to RT slowly overnight. The mixture was diluted with H$_2$O and CH$_2$Cl$_2$, the phases were separated, and the aqueous fraction was extracted several times with CH₂Cl₂. The organic extracts were dried over Na₂SO₄, reduced i. vac, and crystallized from toluene. Recovery from toluene recrystallization is typically 60–85% of the desired salt.

¹H NMR 400 MHz (d6-Acetone) 9.44 (d, 1H, J=1.4 Hz), 9.08 (d, 1H, J=1.2 Hz), 8.14 (m, 1H), 8.04 (t, 1H, J=2.0 Hz), 7.88 (m, 1H), 4.66 (s, 3H), 0.41 (m, 9H), Note: 8.14 and 7.88 ppm multiplets are doublets J=~1.5 Hz, with additional Sn splitting.

mixture was reduced to an oil, and loaded directly onto an E. Merck Lobar B size RP18 (40–63μ) column, filtering if necessary. The product was eluted with CH₃CN: H₂O: 200 mM NH₄Cl aqueous 38:56:6. Product containing fractions were stripped, lyophilized and triturated with dry acetonitrile to filter off NH₄Cl. The ester 7 (651 mg) was obtained as a glass by evaporation i. vac. in 53% yield. The ester obtained is presumed to be the chloride salt.

¹H NMR 400 MHz (CD₃CN:D₂O) 8.83 (d, 1H,

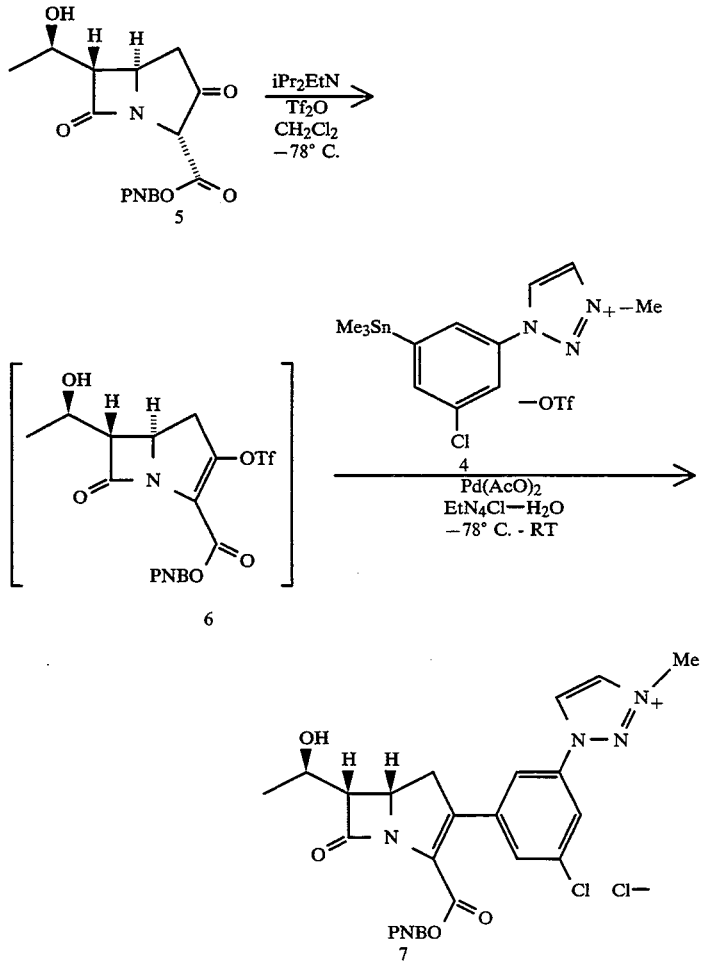

Bicyclic azetidinone 5 (1.0 Eq, 2.2 mmol, 758 mg) was dissolved in distilled CH₂Cl₂ (30 ml) and cooled to −78° C. Neat iPr₂EtN (1.1 Eq, 2.4 mmol, 418 μl) was dropped in to give a bright yellow solution, which was stirred ~5 min at −78° C. Neat trifluoromethanesulfonic anhydride (1.1 Eq, 2.4 mmol, 403 μl) was dropped in to titrate to a colorless solution, which was stirred at −78° C. for twenty minutes. Conversion to the enol triflate, and the subsequent coupling reaction, is monitored by HPLC on an E. Merck LiChrospher 5μ RP-18 analytical column eluting with 65:35 CH₃CN:200 mM NH₄Cl aqueous. After verifying conversion to the enol triflate, the stannane 4 (1.0 Eq, 2.2 mmol, 1.1 g), Et₄N-Cl—H₂O (1.0 Eq, 2.2 mmol, 362 mg), and Pd(AcO)₂ (0.1 Eq, 0.22 mmol, 49 mg) were added as solids, and the reaction mixture warmed to RT in a water bath. Consumption of the starting materials was not complete. The reaction was stopped at two hours. No workup was performed due to the extremely difficult solubility properties of the product salts. The reaction J=1.6 Hz), 8.60 (d, 1H, J=1.6 Hz), 8.09 (d, 2H, J=8.8 Hz), 7.82 (t, 1H, J=2.0 Hz), 7.79 (t, 1H, J=2 Hz), 7.66 (t, 1H, J=1.6 Hz), 7.43 (d, 2H, J=8.8 Hz), 5.22 (Benzylic ABq, 2H, Δδ=37 Hz, J=13.4 Hz), 4.36 (s, 3H), 4.34 (m, 1H, obscured), 4.31 (m, 1H), 4.11 (p, 1H, J=6.3 Hz), 3.40 (dd obscuring ABX, 1H), 3.17–3.45 (AB of ABX, 2H, obscured, J=10.2, 18.6), 1.21 (d, 3H, J=6.3 Hz). Note: ratio of D₂O and CD₃CN affects shifts of peaks at 8.83 and 8.60 ppm.

IR KBr pellet 3400 cm⁻¹ brd, 1775, 1720 cm⁻¹ carbonyls, 1518 cm⁻¹ nitro.

EXAMPLE FIVE

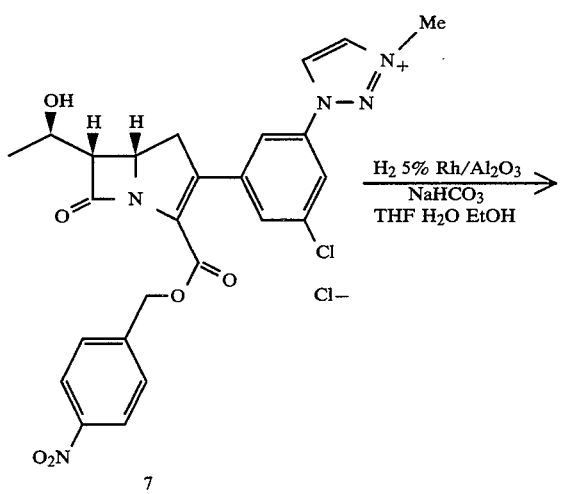

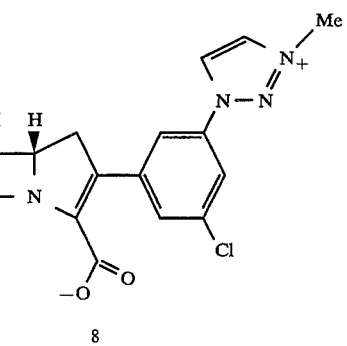

The ester 7 (1.0 Eq, 1.15 mmol, 65 1 mg) was dissolved in 1:1:1 THF:EtOH:H₂O (30 ml) with NaHCO₃ (1.5 Eq, 1.73 mmol, 145 mg) at 0° C. Catalyst, 5% Rh/Al₂O₃ (78 mg, 12% by wt), was added, and the flask flushed three times, vacuum versus H₂. The reaction was stirred at 0° C. under slight H₂ pressure (balloon) until the starting material was consumed. The reaction was monitored by HPLC the column listed above eluting with 46:54 CH₃CN:200 mM NH₄Cl aqueous. An intermediate is commonly observed, with a t½ of ~10 min for conversion to the product. When the starting material is consumed, usually at ~1 hr., the solution is filtered, and the organic solvent removed i. vac. The residue is diluted with water, filtered if necessary, and chromatographed on an E. Merck Lobar B size RP18 (40–63μ) column, eluting with 13:87 CH₃CN:H₂O. The product containing fraction were lyophilized to yield 191 mg (43%) of the desired carbapenem 8. The products are characterized by 400 MHz NMR, IR and extinguished UV. Aliquots are made up in 0.1M MOPS buffer pH=7 at ~1 μM. One sample is quenched with 25 μL 2M NH₂OH HCl. The ε for the extinguished peak at ~306 nm is determined. The expectation values for ε range from 9000–12000.

¹H NMR 400 MHz (D₂O) 9.03 (s, 1H), 8.71 (s, 1H), 7.89 (s, 1H), 7.80 (s, 1H), 7.66 (s, 1H), 4.46 (s, 1H), 4.34 (dt, 1H, J=8.7, 2.6 Hz), 4.26 (p, 1H, J=6.1 Hz), 3.56 (dd, 1H, J=5.9, 2.9 Hz), 3.31 (AB of ABX, 2H, Δδ=123, J=8.5, 9.6, 17 Hz ), 1.30 (d, 3H, J=6.5 Hz).

IR KBr pellet 1751, 1599 cm⁻¹ carbonyls.

UV ε_ext 307 nm 0.1M MOPS pH=7 10800, NH₂OH quenchable.

Preparation of 1,2,4-Triazolium Analogs

EXAMPLE SIX

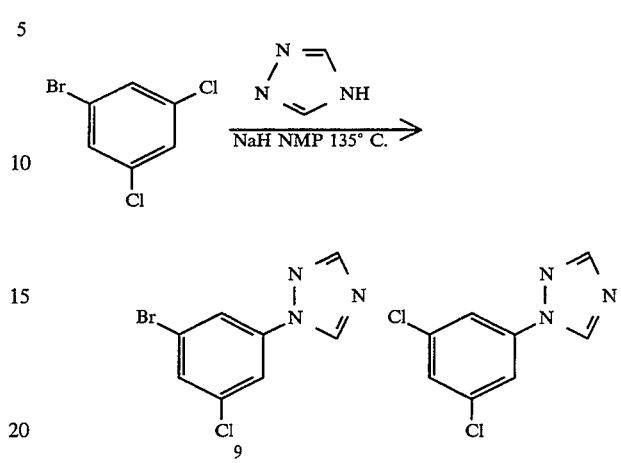

The 1,2,4-triazole 9 was prepared as a mixture with the 3',5'-dichlorophenyl-(1,2,4)triazole, starting from 1-bromo-3,5-dichlorobenzene. Sodium hydride (1.0 Eq, 0.066 mol, 2.66 g, 60% dispersion in oil) was washed three times with hexanes, and dried under a stream of nitrogen. NMP (60 ml) was added, followed by addition of solid 1,2,4-triazole (1.0 Eq, 0.066 mol, 4.5 g). The rate of addition was adjusted to give a manageable gas evolution. The mixture was stirred briefly to give a homogenous solution. Solid 1-bromo-3,5-dichlorobenzene (2.0 Eq, 0.133 mol, 30 g) was added, and the mixture heated to 135° C. for 24 hrs. The reaction mixture was poured into water (600 ml), stirred briefly and filtered. The solid residue was washed with water and air dried. The crude material was purified by chromatography on SiO₂, eluting with toluene:ethyl acetate 96:4. The yield was approximately 60% based on the triazole.

The desired product 9 was obtained as an inseparable mixture, ~1:1 with the dichloro compound. The product was characterized after conversion to the stannane, and removal of the unreacted 3',5'-dichlorophenyl-(1,2,4)triazole. The compound can be prepared as a pure compound as for compound 2 above if desired.

EXAMPLE SEVEN

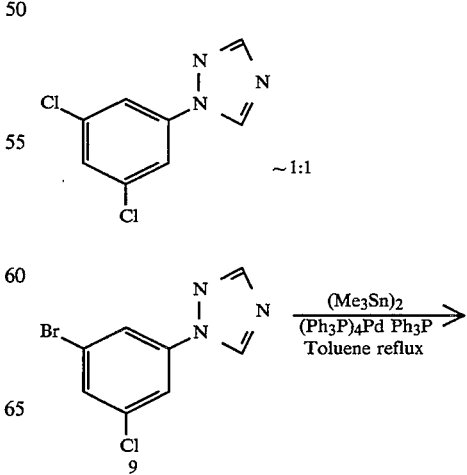

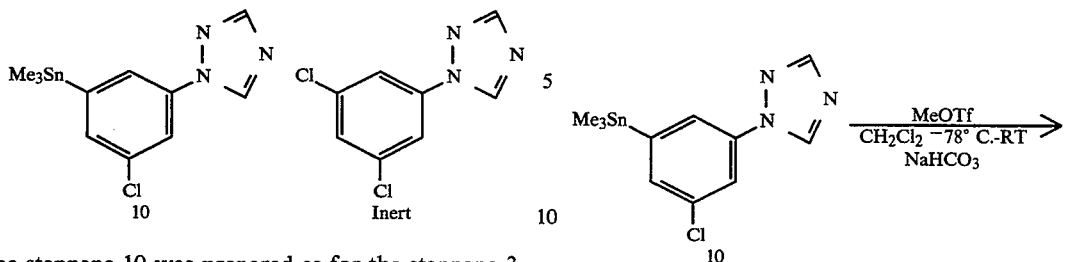

The stannane 10 was prepared as for the stannane 3, using the indicated mixture of the desired bromide, and the inert dichloro compound. From 2.52 g (~9.75 mmol) of starting material and 3.19 g of (Me$_3$Sn)$_2$ (9.75 mmol), 1.68 g of the stannane 10 was obtained as colorless crystal mass after chromatography, for an almost quantitative yield, assuming a 1:1 mixture of starting materials The compound was chromatographed on SiO$_2$ (230 g) eluting with 15% ethyl acetate in hexanes.

$^1$H NMR 400 MHz (d6-Acetone) 9.12 (s, 1H), 8.12 (s, 1H), 7.96 (m, 1H), 7.85 (t, 1H, J=2.1 Hz), 7.54 (m, 1H), 0.35 (m, 9H, J=27.5 Hz). Note: 7.96 and 7.54 ppm multiplets are triplets, J=~1.5 Hz, with additional coupling to Sn.

EXAMPLE EIGHT

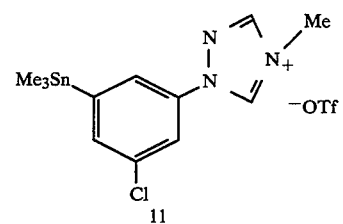

The 1,2,4-triazole 10 was alkylated as for the 1,2,3-triazole above. From 250 mg of the triazole, 305 mg of the desired salt was obtained for an 83% recovery. The salt was recrystallized from toluene, typically in 60-70% recovery.

$^1$H NMR 400 MHz (d6-Acetone) 10.75 (s, 1H), 9.33 (s, 1H), 8.06 (m, 1H), 7.94 (t, 1H, J=2 Hz), 7.80 (m, 1H), 4.31 (s, 3H), 0.47 (m, 9H, J=28 Hz).

EXAMPLE NINE

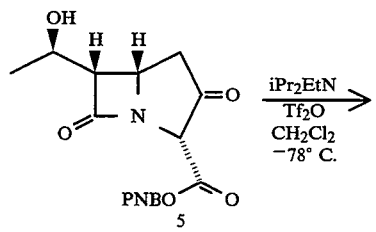

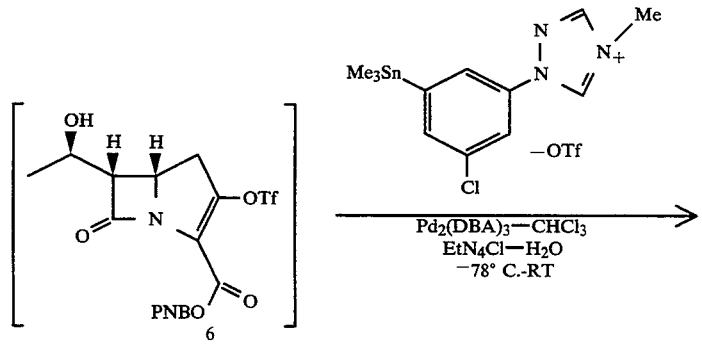

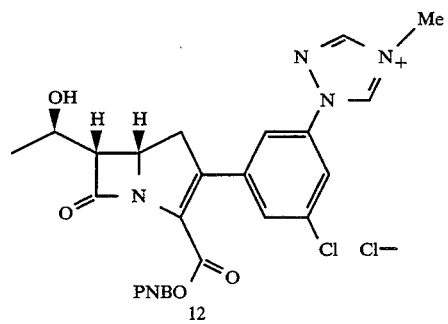

Bicyclic azetidinone 5 (1.0 Eq, 1.1 mmol, 378 mg) was dissolved in distilled CH2Cl2 (10 ml) and cooled to −78° C. Neat iPr2EtN (1.1 Eq, 1.2 mmol, 208 μl) was dropped in to give a bright yellow solution, which was stirred ~5 min at −78° C. Neat trifluoromethanesulfonic anhydride (1.1 Eq, 1.2 mmol, 201 μl) was dropped in to titrate to a colorless solution, which was stirred at −78° C. for twenty minutes. Conversion to the enol triflate, and the subsequent coupling reaction, is monitored by HPLC on an E. Merck LiChrospher 5μ RP-18 analytical column eluting with 65:35 CH3CN:200 mM NH4Cl aqueous. After verifying conversion to the enol triflate, the stannane 11 (1.0 Eq, 1.1 mmol, 550 mg) and Pd2DBA3—CHCl3 (0.1 Eq, 0.11 mmol, 112 mg) were added as solids, followed by 1 Vol. (10 ml) of NMP. The reaction mixture warmed to RT in a water bath. Consumption of starting materials was monitored by HPLC. The reaction mixtures were stripped after 1 hr, and the residue precipitated into 10-12 volumes of ether to remove NMP. The precipitate was loaded directly onto an E. Merck Lobar B size RP 18 (40–63μ) column, filtering if necessary. The product was eluted with CH3CN:20 mm NH4Cl aqueous 40:60. Product containing fractions were stripped, lyophilized and triturated with dry acetonitrile to filter off NH4Cl. The ester 12 (257 mg) was obtained as a glass by evaporation i. vac. in 41% yield. The ester obtained is presumed to be the chloride salt.

$^1$H NMR 300 MHz (d6-Acetone:D2O) 9.13 (s, 1H), 8.06 (d, 2H, J=8.9 Hz), 7.86 (t, 1H, J=2.1 Hz), 7.83 (t, 1H, J=2 Hz), 7.58 (t, 1H, J=1.6 Hz), 7.46 (d, 2H, J=8.9 Hz), 5.24 (Benzylic ABq, 2H, Δδ=32.5 Hz, J=13.5 Hz), 4.46 (s, 3H), 4.33 (m, 1H), 4.12 (m obscured by HOD), 3.47 (dd, 1H, J=6.6, 3.0 Hz), 3.39 (AB of ABX, 2H, Δδ=66.9 Hz, J=8.5, 10.3, 18.7 Hz), 1.22 (d, 3H, J=6.4 Hz) Note: Triazolium 5H exchanges out in D2O, observed at 11.14 ppm in dry d6-Acetone. Solubility is poor in dry solvent.

IR KBr pellet 3390 cm$^{-1}$ brd, 1772, 1721 cm$^{-1}$ carbonyls, 1518 cm$^{-1}$ nitro.

EXAMPLE TEN

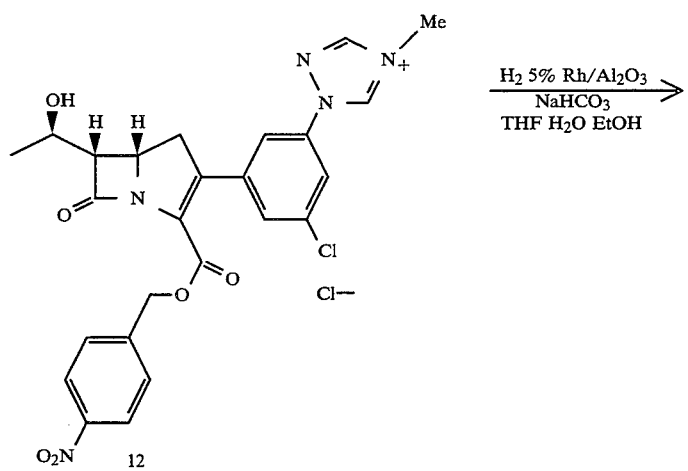

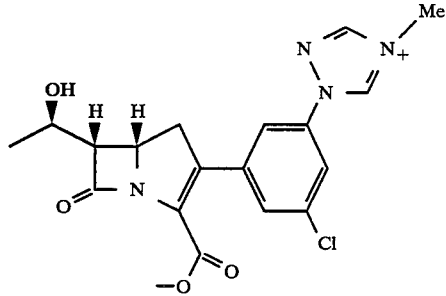

13

The cleavage of the p-nitrobenzyl ester 12 was run as for the ester 7 above. Analytical and preparative columns are as for the above. The reaction was monitored with 50:50 CH$_3$CN:200 mM NH$_4$Cl, and the final product purified with 14:86 CH$_3$CN:H$_2$O. From 257 mg of the ester 12, 79 mg of the zwitterion 13 is obtained as a lyophilizate, for a yield of 45% of the theoretical.

1H NMR 300 MHz (D$_2$O) 9.05 (s, 1H), 7.87 (t, 1H, J=1.9 Hz), 7.76 (t, 1H, J=1.7 Hz), 7.63 (t, 1H, J=1.7 Hz), 4.37 (m, 1H), 4.30 (p, 1H, J=6.2 Hz), 4.13 (s, 3H), 3.60 (dd, 1H, J=5.9, 3 Hz), 3.35 (AB of ABX, 2 H, Δδ=95.85, J=8.5, 9.9, 17.0), 1.34 (d, 3H, J=6.4). Note: Triazolium 5-H is exchanged out.

IR KBr pellet 1751, 1597–1599 cm$^{-1}$ carbonyls.

UV $\epsilon_{ext}$ 307 nm 0.1M MOPS pH=7 11100, NH$_2$OH quenchable.

Preparation of Tetrazolium Analogs

EXAMPLE ELEVEN

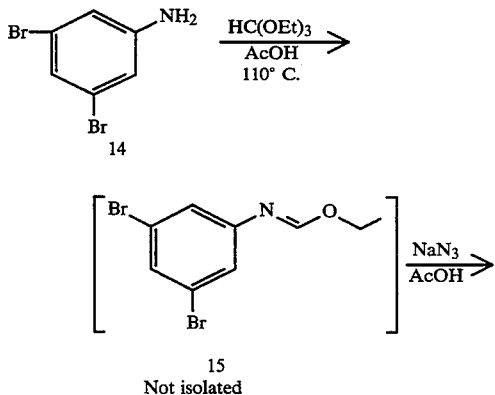

15
Not isolated

16

The 3,5-dibromoaniline (1.0 Eq, 4 mmol, 1 g) was dissolved in triethylorthoformate (1.1 Eq, 4.4 mmol, 0.73 ml), and a catalytic quantity (0.1 Eq, 0.4 mmol, 24 μl) of acetic acid added. The mixture was heated to 110° C., with the immediate distillation of ethanol. The mixture was heated for one hour, cooled, and as much as possible of the orthoformate removed i. vac. The mixture was diluted with acetic acid (10 ml), at which point a solid precipitates. Solid NaN$_3$ (4.0 Eq, 16 mmol, 1.04 g) was added, and the mixture stirred 20 hrs. The conversion to the product is monitored on SiO$_2$ analytical plates eluting with 8:1:1 hexanes:ethyl acetate:CH$_2$Cl$_2$. The reaction mixture was diluted with H$_2$O and CH$_2$Cl$_2$, extracted 3 times with CH$_2$Cl$_2$, and the combined organic phases washed with brine. The CH$_2$Cl$_2$ phase was dried over Na$_2$SO$_4$, and reduced i. vac. The residue was chromatographed on SiO$_2$ (40 g) eluting with CCl$_4$ ethyl acetate 81:9. The desired tetrazole 16 (766 mg, 63% of the theoretical) is obtained as a crystalline solid.

$^1$H NMR 200 MHz (CDCl$_3$) 9.01 (s, 1H), 7.88 (d, 2H, J=1.5 Hz), 7.85 (m, 1H).

IR (CHCl$_3$ soln.) Featureless above 1590 cm.$^{-1}$, 1590, 1575 cm$^{-1}$, 1480 cm$^{-1}$ all str.

EXAMPLE TWELVE

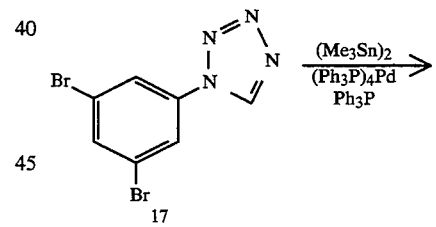

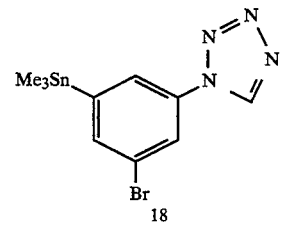

The bromide 17 is converted to the stannane 18 as for the bromide 2, except for the use of 1.0 Eq of (Me$_3$Sn)$_2$. From 500 mg of the bromide 17, 185 mg (29%) of the stannane 18 was obtained, along with 200 mg (40%) recovered starting material (48% based on consumed SM). The product was purified on SiO$_2$ (50 g) eluting with Ethyl acetate in CCl$_4$ 9:81. No bis-stannylated product was observed.

$^1$H NMR 300 MHz (CDCl$_3$) 8.97 (s, 1H), 7.77 (t, 1H, J=1.9 Hz), 7.71 (m, 1H), 7.69 (m, 1H), 0.37 (m, 9H, J=26.92).

EXAMPLE THIRTEEN

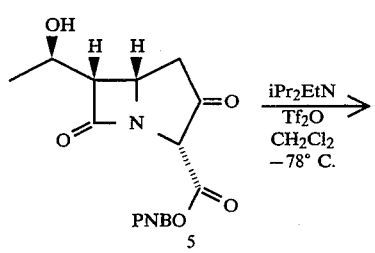

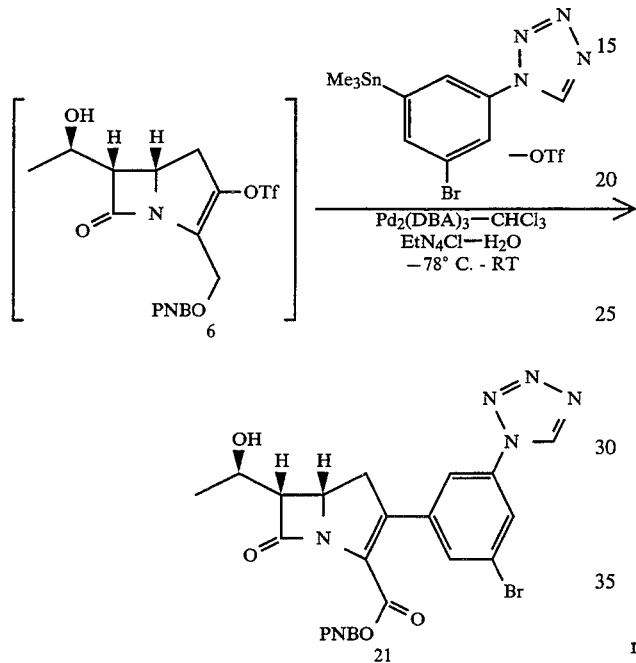

The coupling of the tetrazolyl stannane 18 and the bicyclic azetidinone 5 was run as for the triazolium stannane 11 above. From 89 mg of the azetidinone and 100 mg of the stannane 18 (0.26 mmol), 38 mg (0.07 mmol, 27%) of the 2-arylcarbapenem 21 was recovered. The product was purified by chromatography on $SiO_2$ (8 g), eluting with $CH_2Cl_2$ ethyl acetate 60:40. The product was obtained as an oil.

$^1$H NMR 400 MHz (d6-Acetone) 9.75 (s, 1H), 8.15 (d, 2H, J=8.8 Hz), 8.08 (t, 1H, J=1.9 Hz), 8.02 (t, 1H, J=1.5 Hz), 7.81 (t, 1H, J=1.6 Hz), 7.62 (d, 2H, J=9 Hz), 5.34 (Benzylic ABq, 2H, Δδ=52.7 Hz, J=13.8 Hz), 4.42 (m, 1H, J=8.4, 3.0 Hz), 4.18 (sxt, 1H, J=5.1 Hz), 3.51 (AB of ABX, 2H, Δδ=115.8 Hz, J=8.4, 10.3, 18,4 Hz),3.48 (dd, 1H, J=3.1, 6.4 Hz), 1.28 (d, 3H, J=6.3 Hz).

EXAMPLE FOURTEEN

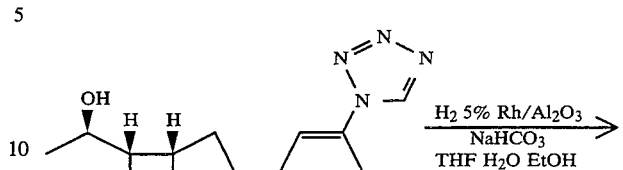

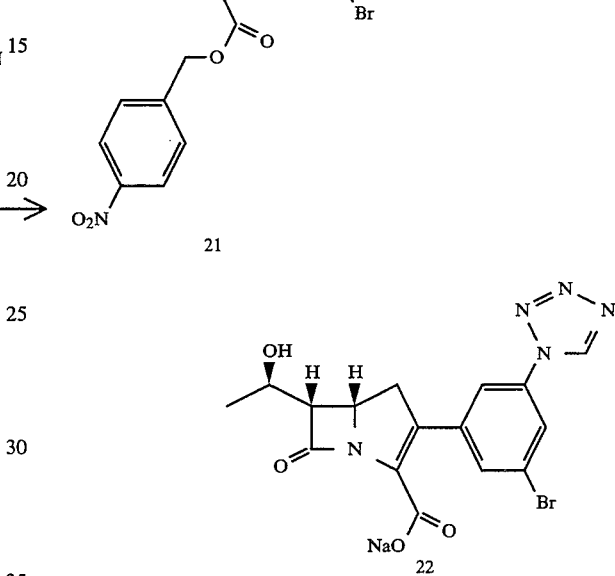

The deprotection of the p-nitrobenzyl ester 21 was run as for the compounds 7 and 12 above. The ester 21 (38 mg) was dissolved in 3 ml of solvent. The product was purified on an E. Merck Lobar A size RP-18 (40–63μ) column to yield 8 mg (28%) of the sodium salt 22.

$^1$H NMR 400 MHz ($D_2O$) 9.97 (s, 1H), 8.25 (s, 1H), 8.09 (s, 1H), 8.06 (s, 1H), 4.6 (m, 1H, part. obscured HOD), 4.51 (p, 1H, J=6.2 Hz), 3.77 (dd, 1H, J=2.6, 5.9 Hz), 3.57 (AB of ABX, 2H, Δδ=116.9, J=8.26, 9.97, 16.7 Hz), 1.57 (d, 3H, J=6.4 Hz).

UV $\epsilon_{ext}$ 306 nm 0.1 M MOPS pH=7 8130, $NH_2OH$ quenchable.

Using the general synthesis schemes and Examples provided above, the starting materials shown below in columns one, three and four of the Table can be used in the schemes designated to provide the compounds shown.

TABLE
| Aryl starting Material | Scheme (Nucleophile) | Alkylating Agent Rb—X | Product Scheme IV |
|---|---|---|---|
| 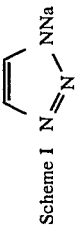 | Scheme I 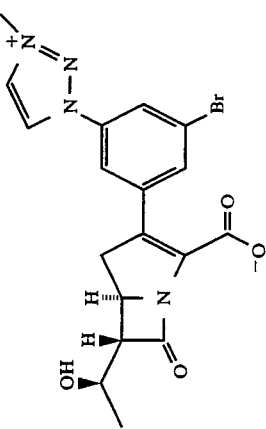 | Scheme III<br>MeOTf | 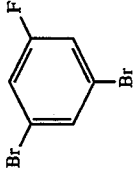 |
| 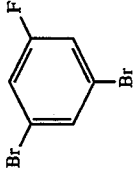 | Scheme I 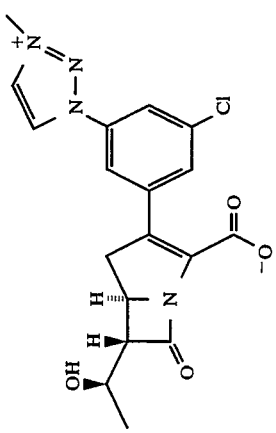 | MeOTf | 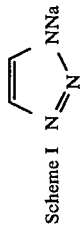 |
| 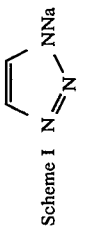 | Scheme I 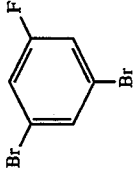 | MeOTf | 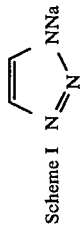 |

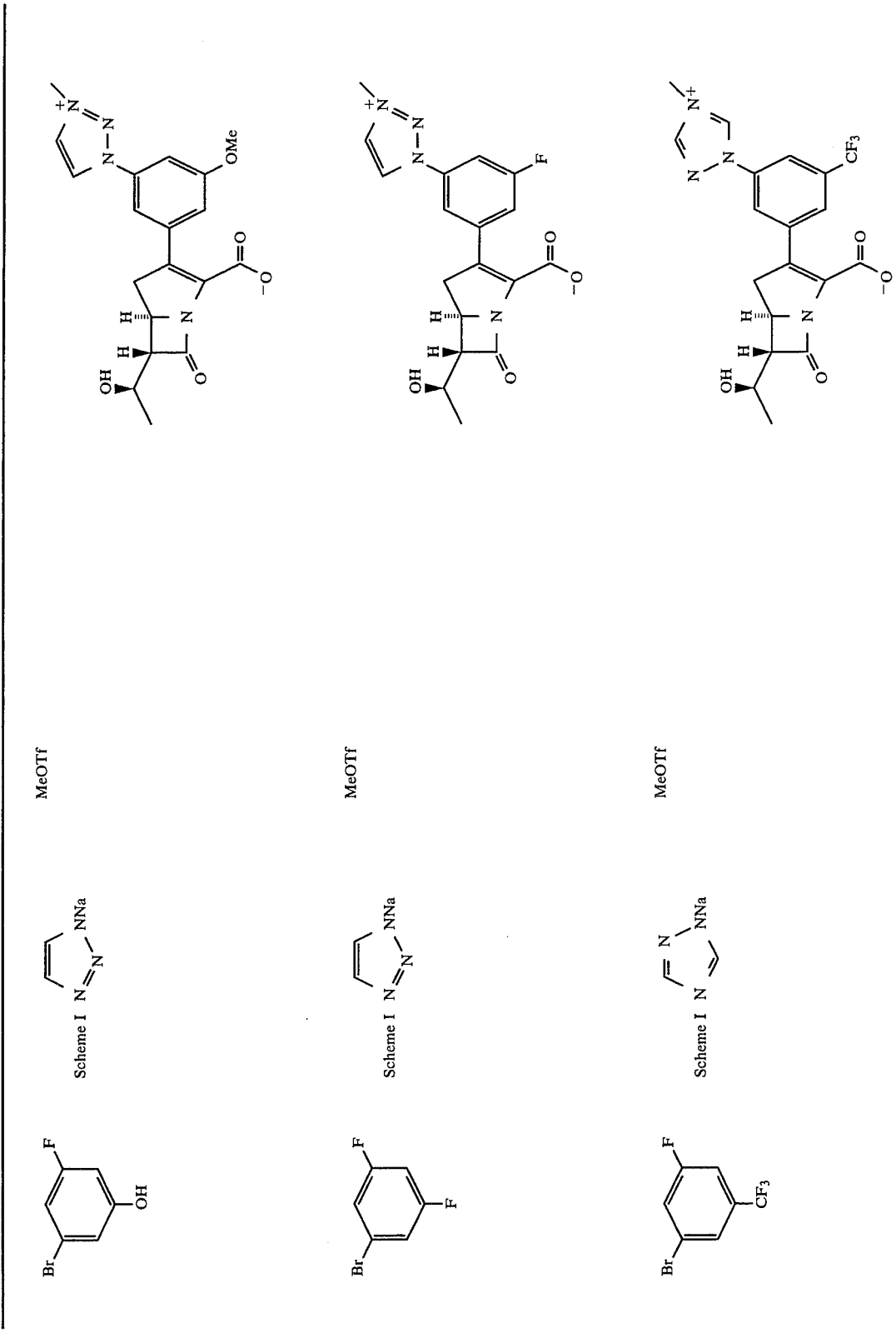

TABLE-continued
| | Scheme I | MeOTf | |
|---|---|---|---|
| 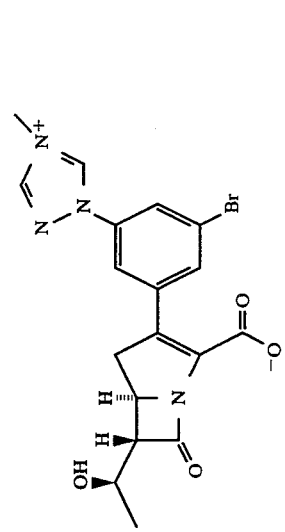 | 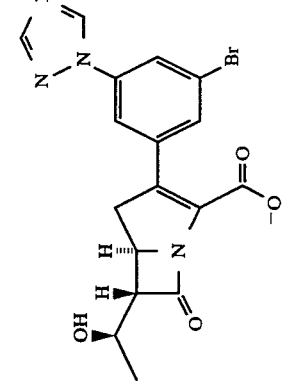 | | 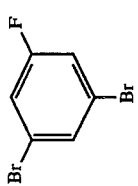 |
| 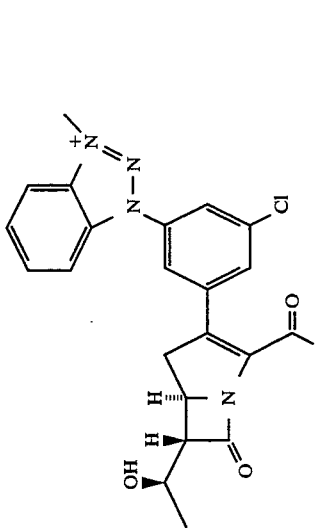 | 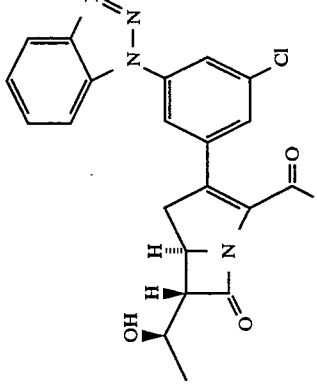 | | 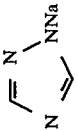 |
| 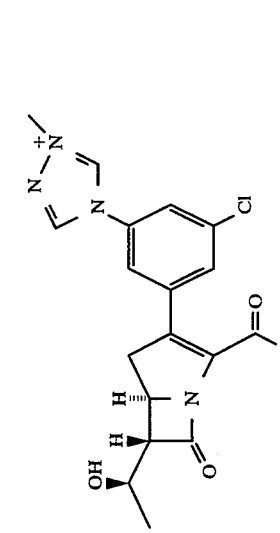 | 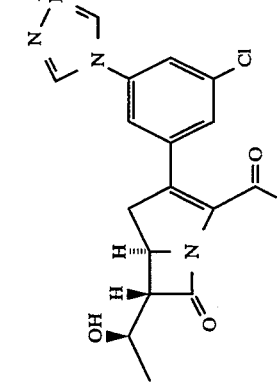 | | 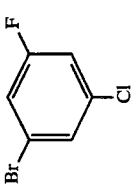 |

TABLE-continued
| | | | |
|---|---|---|---|
|  | 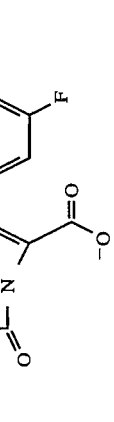 Scheme I | MeOTf |  |
| 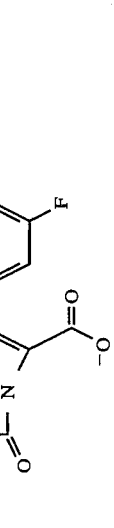 |  Scheme I | MeOTf |  |
|  |  Scheme I | MeOTf |  |

TABLE-continued
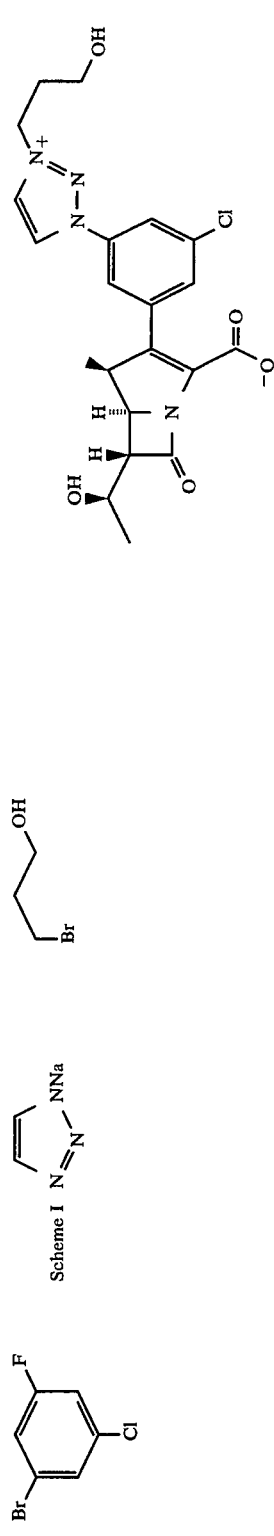
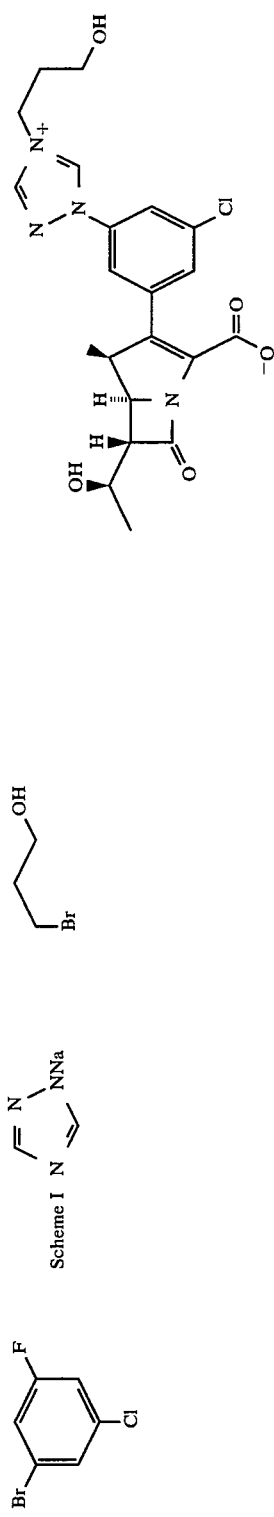
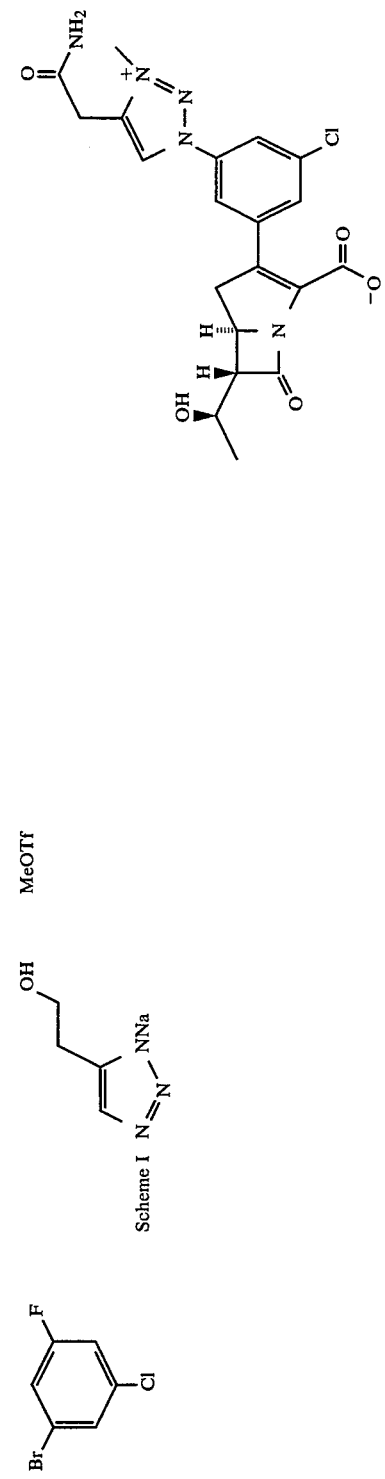

TABLE-continued

TABLE-continued

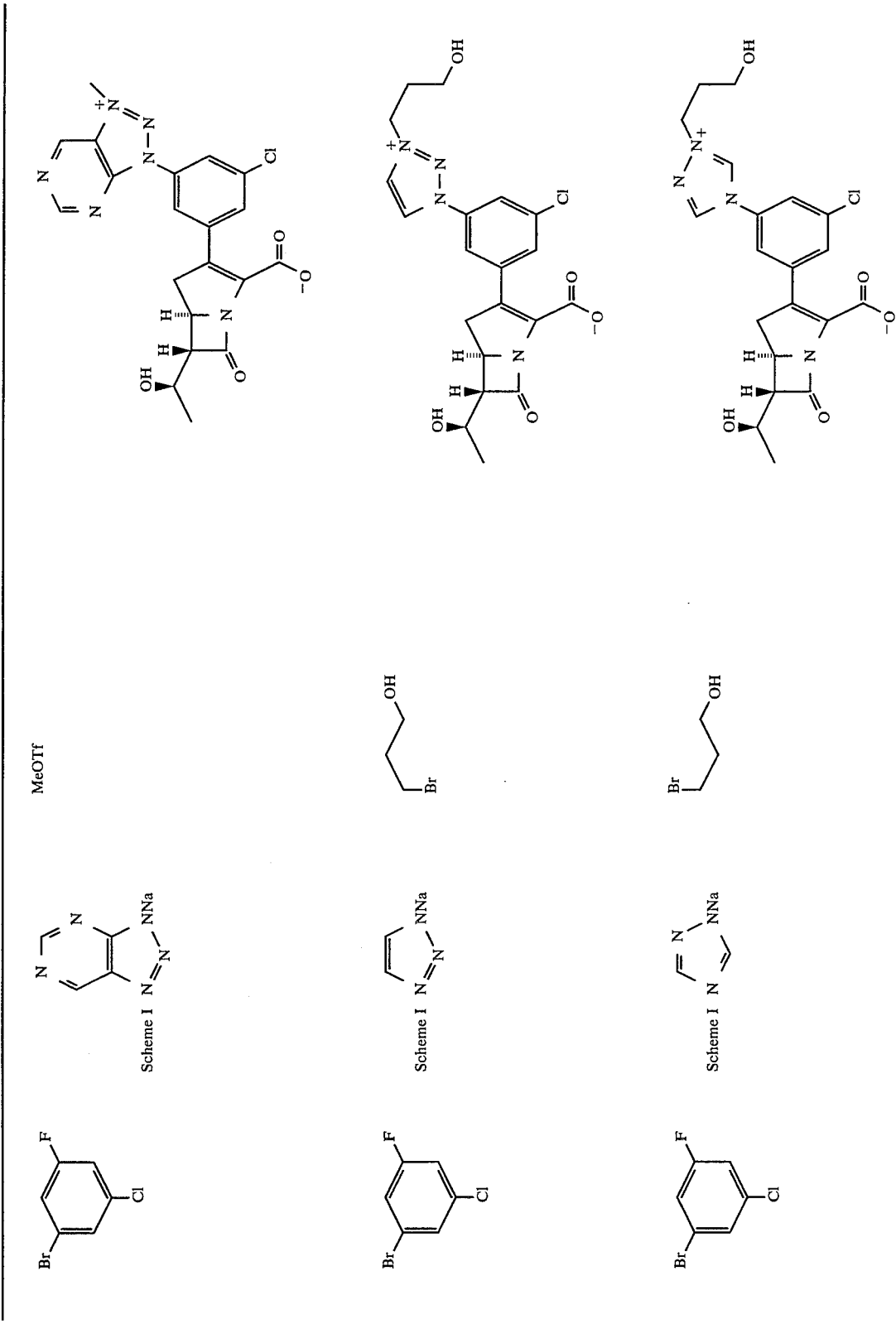

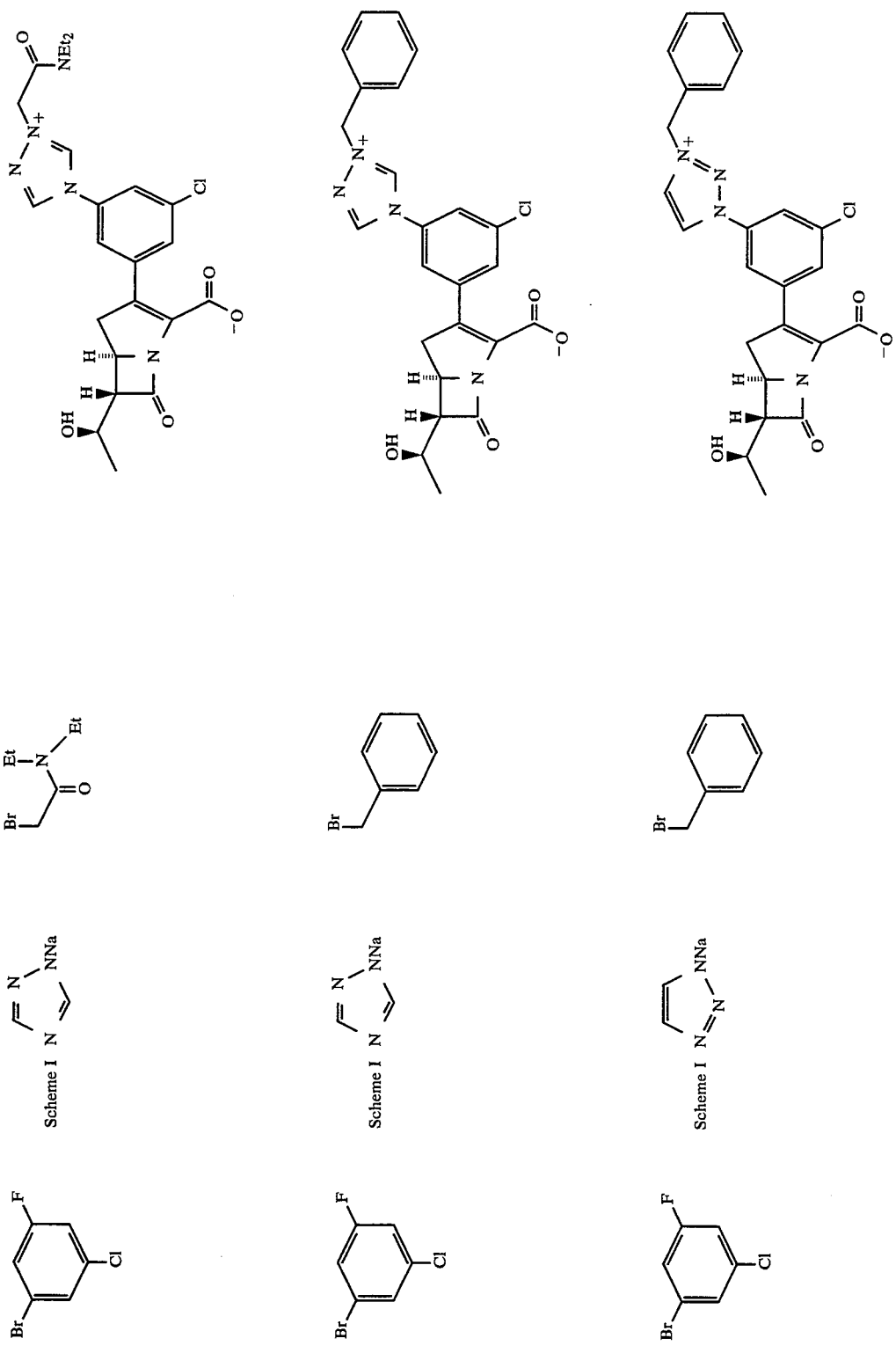

TABLE-continued

| Starting Material | Scheme | Reagent | Product |
|---|---|---|---|
| 4-NO₂, 2-OCF₃ aniline | Scheme II via Azide | MeOTf | carbapenem with 3-(1-methyl-1,2,3-triazolium)-5-OCF₃-phenyl |
| 4-NO₂, 2-OCF₃ aniline | Scheme II via Hydrazine | MeOTf | carbapenem with 3-(1-methyl-1,2,3-triazolium)-5-OCF₃-phenyl |
| 4-NO₂, 2-SCF₃ aniline | Scheme II via Azide | MeOTf | carbapenem with 3-(1-methyl-1,2,3-triazolium)-5-SCF₃-phenyl |

TABLE-continued

| | | |
|---|---|---|
| NO₂, SCF₃, H₂N (structure) | Scheme II via Hydrazine | MeOTf |
| NO₂, CN, H₂N (structure) | Scheme II via Azide | MeOTf |
| NO₂, CN, H₂N (structure) | Scheme II via Hydrazine | MeOTf |

TABLE-continued
| | | | |
|---|---|---|---|
| 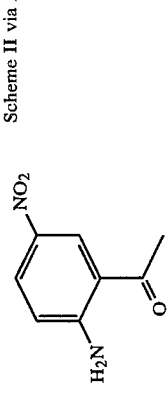 | Scheme II via Azide | MeOTf | 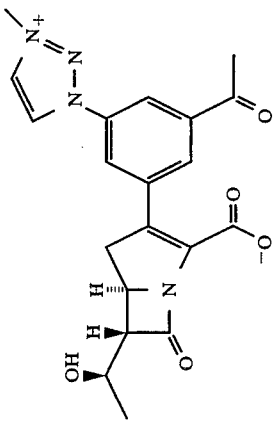 |
| 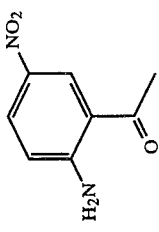 | Scheme II via Hydrazine | MeOTf | 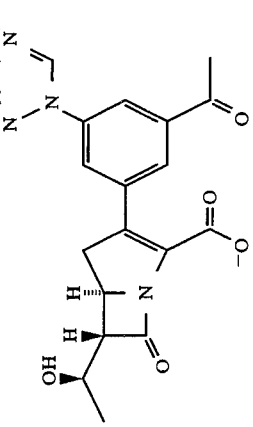 |
| 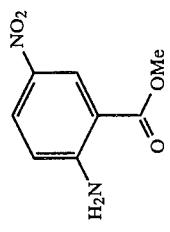 | Scheme II via Hydrazine | MeOTf | 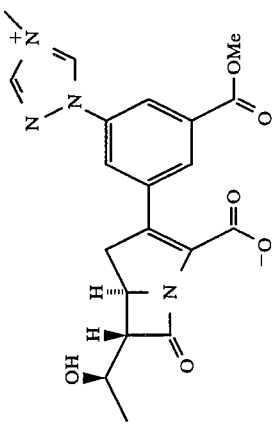 |

TABLE-continued
| | | |
|---|---|---|
| 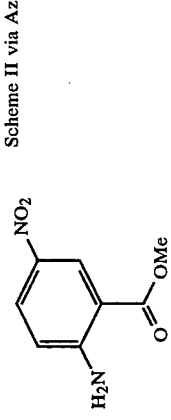 | Scheme II via Azide | MeOTf |
| 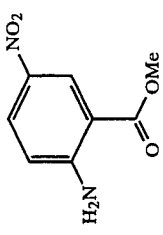 | Scheme II via Hydrazine | MeOTf |
| 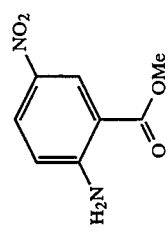 | Scheme II via Azide | MeOTf |
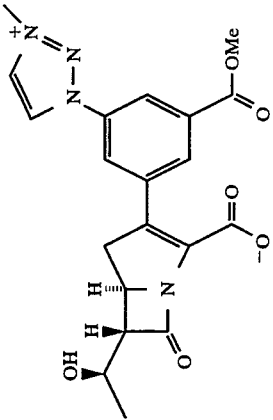
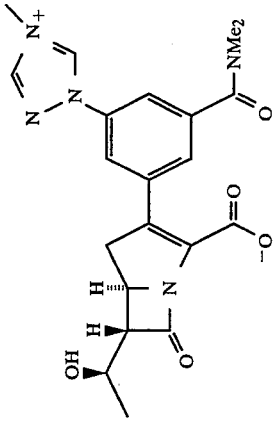
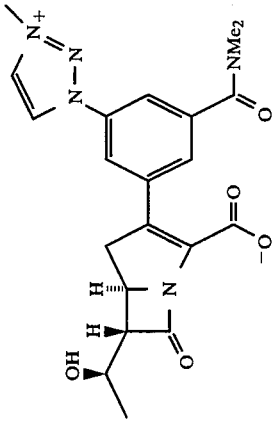

TABLE-continued

| | Scheme II via Hydrazine | MeOTf |
| | Scheme II via Azide | MeOTf |
| | Scheme II via Hydrazine | MeOTf |

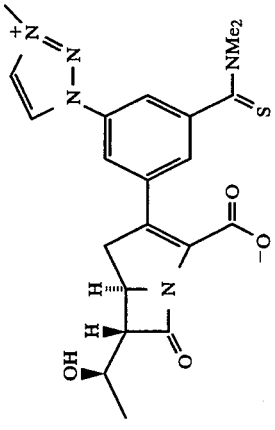

TABLE-continued

| | | |
|---|---|---|
| NO2 / CN / NH2 | Scheme II via Azide | MeOTf |
| NO2 / CN / NH2 | Scheme II via Hydrazine | MeOTf |
| NO2 / O2S-Me / NH2 | Scheme II via Azide | MeOTf |

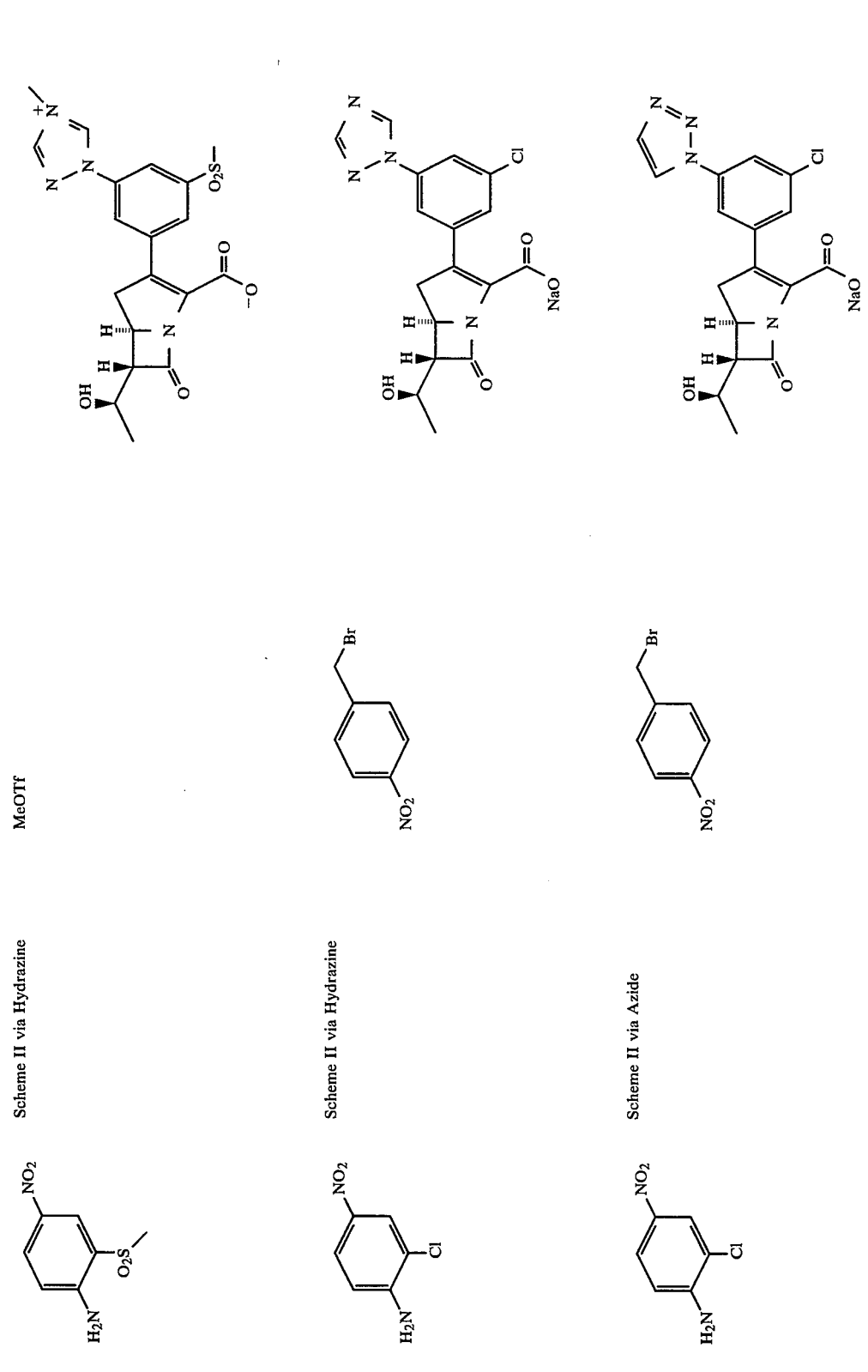

| Starting Materials | Scheme | Alkylating Agent | End Product |
|---|---|---|---|
| 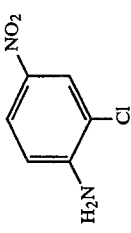 2-chloro-4-nitroaniline | Scheme V via aniline | Not present | 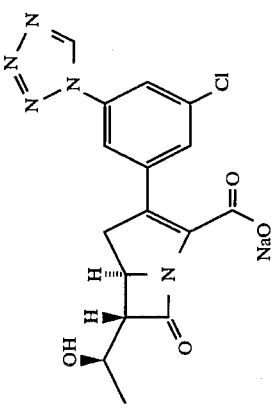 |
| 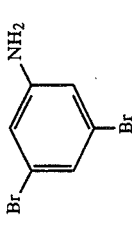 3,5-dibromoaniline | Scheme V | Not Present | 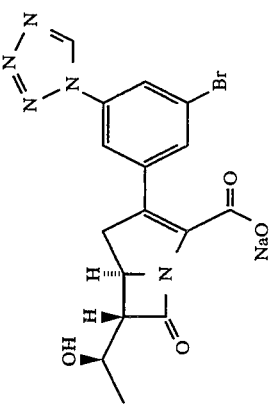 |
| 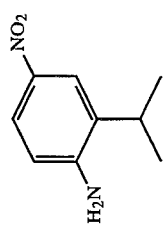 2-isopropyl-4-nitroaniline | Scheme V via aniline | Not Present | 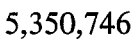 |

TABLE-continued
| | | | |
|---|---|---|---|
|  | Scheme V via Aniline | MeOTf | 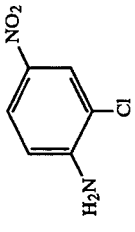 |
| 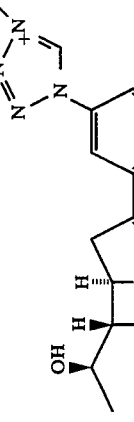 | Scheme V via Aniline | MeOTf | 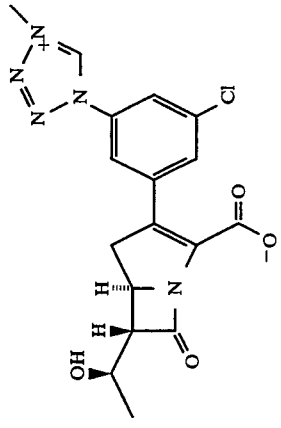 |
|  | Scheme V via Aniline | MeOTf | 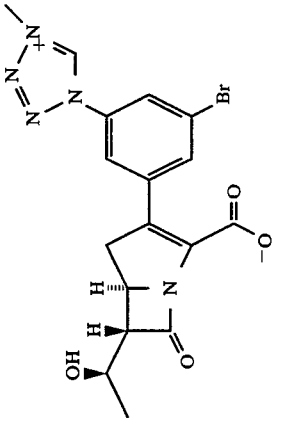 |
Alkylating Agent in Scheme VI TABLE-continued
| Aryl starting Material | Scheme | Alkylating Agent Rb—X | Product Scheme IV |
|---|---|---|---|
| 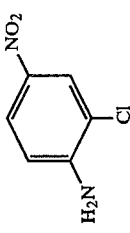 | Scheme VI via Hydrazine | MeOTf | 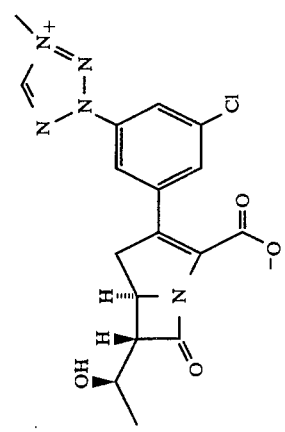 |
| Aryl starting Material | Scheme | Alkylating Agent Rb—X | Product |
|---|---|---|---|
| | | Scheme VI | |
| 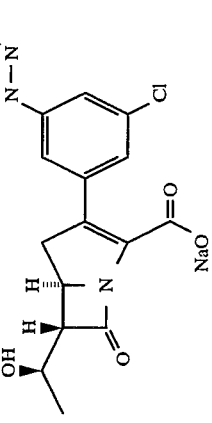 | Scheme VI via Hydrazine | Not Present | 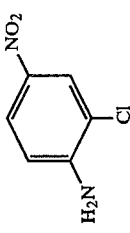 |
| 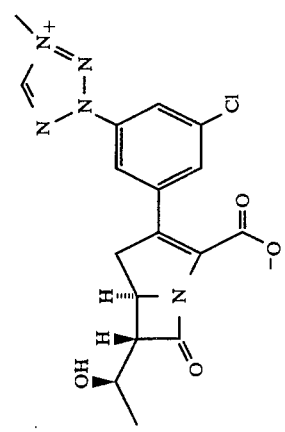 | Scheme VI | Not Present | 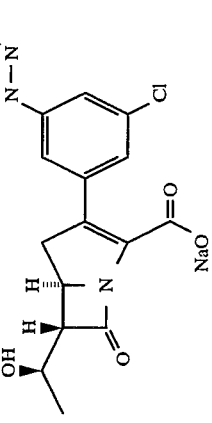 |

TABLE-continued
| Starting Materials | Scheme | Alkylating Agent | End Product |
|---|---|---|---|
| 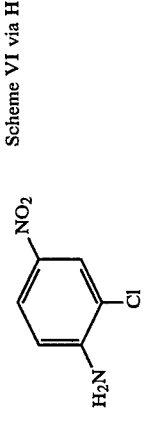 | Scheme VI via Hydrazine |  | 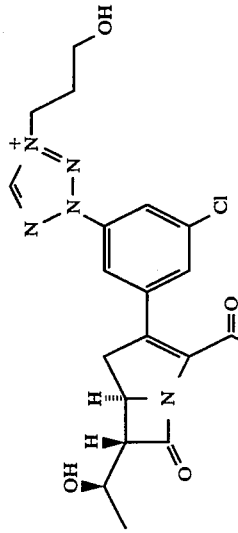 |
Scheme V via Aniline
| Starting Materials | Scheme | Alkylating Agent | End Product |
|---|---|---|---|
| 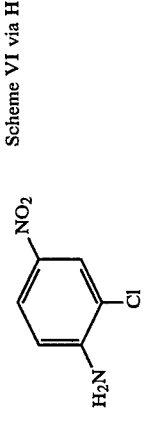 | Scheme V via Aniline | 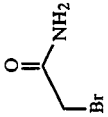 | (see above) |
Scheme VI via Hydrazine
| Starting Materials | Scheme | Alkylating Agent | End Product |
|---|---|---|---|
| 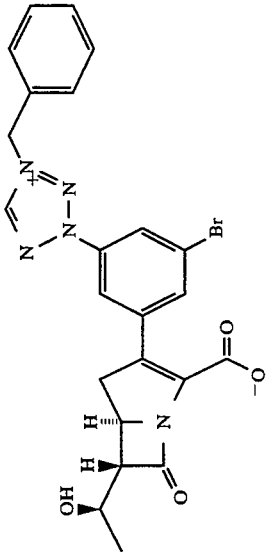 | Scheme VI via Hydrazine | (benzyl bromide) | (see above) |

TABLE-continued

| Scheme VI via Hydrazine | | |
|---|---|---|
| ![structure: 3-chloro-4-aminonitrobenzene] | ![structure: bromoacetamide] | ![structure: carbapenem with triazolium-aryl-Br substituent] |

What is claimed is:

1. A triazolyl or tetrazolyl phenyl substituted carbapenem represented by formula I

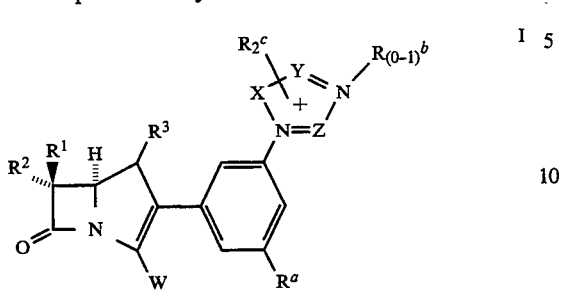

or a pharmaceutically acceptable salt thereof, wherein:
$R^1$ and $R^2$ independently represent H, $CH_3-$, $CH_3CH_2-$, $(CH_3)_2CH-$, $HOCH_2-$, $CH_3CH(OH)-$, $(CH_3)_2C(OH)-$, $FCH_2CH(OH)-$, $F_2CHCH(OH)-$, $F_3CCH(OH)-$, $CH_3CH(F)-$, $CH_3CF_2-$ or $(CH_3)_2CF-$;
$R^3$ is H or methyl:
$R^a$ is H or is selected from the group consisting of
a) $-CF_3$;
b) a halogen atom selected from the group consisting of: $-Br$, $-Cl$, $-F$ and $-I$;
c) $-OH$;
d) $-OC1-4$ alkyl, wherein the alkyl is optionally mono-substituted by Rq, where Rq is selected from the group consisting of $-OH$, $-OCH_3$, $-COOM$, with M representing H, a negative charge, a metal cation or an ester forming group;
e) $-NR'R''$ wherein R' and R'' independently represent H or C1-4 alkyl;
f) $-S(O)_n-R^s$, where n=0-2, and $R^s$ is C1-4 alkyl or phenyl, each of which is optionally mono-substituted by $R^q$ as defined above;
g) $-CN$;
h) $-C(O)H$ or $-CH(OCH_3)_2$;
i) $-C(O)R^s$, where $R^s$ is as defined above;
j) $-C(O)OC1-4$ alkyl, where the alkyl is optionally mono-substituted by $R^q$ as defined above;
k) $-C(O)N(R^y)R^z$, where $R^y$ and $R^z$ are independently H, C1-4 alkyl, (optionally mono-substituted by $R^q$ as defined above), or $N(R^y)R^z$ are taken together to represent an amino acid residue, or are taken together to represent a 4- to 5-membered alkylidene radical which forms a ring (optionally substituted with $R^q$ as defined above), or a 3- to 4-membered alkylidene radical interrupted by $-O-$, $-S-$, $-S(O)-$ or $-S(O)_2-$ which forms a ring;
l) $-C(S)N(R^y)R^z$ where $R^y$ and $R^z$ are as defined above;
m) $-SCN$;
n) $-SCF_3$;
o) $-OCF_3$;
p) tetrazolyl, where the point of attachment is the carbon atom of the tetrazole ring and one of the nitrogen atoms is mono-substituted by hydrogen, an alkali metal or a C1-C4 alkyl;
q) a C2-C4 alkenyl radical, optionally mono-substituted by one of the substituents a) to p) above and phenyl which is optionally substituted by $R^q$ as defined above:
r) a C2-C4 alkynyl radical, optionally mono-substituted by one of the substituents a) to q) above;
s) a C1-C4 alkyl radical;
t) a C1-C4 alkyl group substituted with 1-3 groups $R^q$ as defined above, or mono-substituted by one of the substituents a)-s) above;

$R^b$ is present or absent; when $R^b$ is absent, the nitrogen to which said group is shown optionally attached is uncharged; when $R^b$ is present, $R^b$ is selected from the group consisting of:
(a) $-C_{1-4}$ alkyl; (b) $-NR'R''$ with R' and R'' equal to H or $C_{1-4}$ alkyl and (c) $C_{1-4}$ alkyl substituted with up to three groups selected from:
hydroxy;
C1-4 alkoxy;
phenyl, nitrophenyl, methoxyphenyl or dimethoxyphenyl;
heteroaryl;
heteroaryl substituted with $R^s$, as defined above;
$-NR'R''$, with R' and R'' as defined above;
$-OC(O)R^s$, where $R^s$ is $C_{1-4}$ alkyl or phenyl, each of which is optionally mono-substituted by $R^q$ as defined above;
$-C(O)-R^s$ with $R^s$ as previously defined;
$-C(O)N(R^y)R^z$, where $R^y$ and $R^z$ are as defined above;
$-C(O)OC_{1-4}$ alkyl, where the alkyl is optionally mono-substituted by $R^q$ as defined above; and
COOM, with M as defined above;
one or two of X, Y and Z represent a N atom and the other variables are carbon atoms;
each $R^c$ is independently selected from the group consisting of hydrogen, halo, C1-4 alkyl, $-COOM$ with M as previously defined, and C1-4 alkyl substituted with from 1 to 3 groups selected from:
hydroxy;
$-C(O)-Rs$ with Rs as previously defined;
COOM, with M as previously defined;
$-O-(C1-4)$ alkyl, wherein the alkyl portion is optionally substituted with Rq, as defined above;
$-NR'R''$, with R' and R'' as defined above;
$-C(O)O(C1-4)$ alkyl, where the alkyl portion is optionally mono-substituted with Rq as defined above;
$-C(O)N(R^y)R^z$, where $R^y$ and $R^z$ are independently H, C1-4 alkyl (optionally mono-substituted by $R^q$ as defined above), or $N(R^y)R^z$ are taken together to represent an amino acid residue, or are taken together to represent a 4- to 5-membered alkylidene radical which forms a ring (optionally substituted with $R^q$ as defined above), or a 3- to 4-membered alkylidene radical interrupted by $-O-$, $-S-$, $-S(O)-$ or $-S(O)_2-$ which forms a ring;
$-OC(O)N(R^y)R^z$, where $R^y$ and $R^z$ are as defined above:
alternatively, the two $R^c$ groups may be taken in combination to represent an aromatic ring fused to the ring to which they are attached, said aromatic 5-6 membered ring selected from the group consisting of phenyl, pyridine, pyrazine, pyrimidine, pyrrole, imidazole, thiophene, furan and thiazole;
W is selected from: $-COOH$, or a pharmaceutically acceptable salt or ester thereof; COORP where RP is a readily removable carboxyl covering group which is not a pharmaceutically acceptable ester; $COOM^a$ where $M^a$ is an alkali metal, or a negative charge.

2. A compound in accordance with claim 1, wherein $R^1$ is hydrogen and $R^2$ is (R)CH$_3$CH(OH)— or (R)CH$_3$CH(F)—.

3. A compound in accordance with claim 1 wherein $R^3$ represents a beta methyl substituent group.

4. A compound in accordance with claim 1 wherein the triazole or tetrazole ting attached to the phenyl group at position 3' is uncharged.

5. A compound in accordance with claim 1 wherein the triazole or tetrazole ting attached to the phenyl group at position 3' is positively charged.

6. A compound in accordance with claim 1 wherein $R^a$ is selected from the group consisting of:
  a) —CF$_3$;
  b) a halogen atom selected from the group consisting of: —Br, —Cl, —F and —I;
  c) —OH;
  d) —OC1–4 alkyl;
  e) —NR'R" wherein R' and R" independently represent H or C1–4 alkyl;
  f) —S(O)$_n$—R$^s$, where n=0–2, and R$^s$ is C1–4 alkyl or phenyl, each of which is optionally mono-substituted by R$^q$ as defined above;
  g) —CN;
  h) —C(O)R$^s$, where R$^s$ is selected from the group consisting of —OH, —OCH$_3$, —COOM, with M representing H, a negative charge, a metal cation or an ester forming group;
  i) —C(O)OC1–4 alkyl where the alkyl is optionally mono-substituted by R$^q$ as defined above;
  j) —C(O)N(R$^y$)R$^z$, where R$^y$ and R$^z$ are independently H, C1–4 alkyl (optionally mono-substituted by R$^q$ as defined above), or are taken in combination with the N to which they are attached to represent an amino acid residue, or are taken together to represent a 4- to 5-membered alkylidene radical which forms a ring (optionally substituted with R$^q$ as defined above), or a 3- to 4-membered alkylidene radical interrupted by —O—, —S—, —S(O)— or —S(O)$_2$— which forms a ring;
  k) —C(S)N(R$^y$)R$^z$ where R$^y$ and R$^z$ are as defined above independently or in combination with the nitrogen to which they are attached;
  l) —SCF$_3$;
  m) —OCF$_3$;
  n) tetrazolyl, where the point of attachment is the carbon atom of the tetrazole ring and one of the nitrogen atoms is mono-substituted by hydrogen, an alkali metal or a C1–C4 alkyl;
  o) a C1–C4 alkyl radical, and
  p) a C1–C4 alkyl group substituted with 1–3 groups R$^q$ as defined above, or mono-substituted by one of the substituents a)–o) above.

7. A compound in accordance with claim 6 wherein $R^1$ represents hydrogen, $R^2$ represents (R)CH$_3$CH(OH)— or (R)CH$_3$CH(F)— and $R^3$ represents a beta methyl substituent group.

8. A compound in accordance with claim 7 wherein W is selected from: —COOH or a pharmaceutically acceptable salt or ester thereof, COOM$^a$ where M$^a$ represents an alkali metal cation or a negative charge.

9. A compound in accordance with claim 1 wherein the two R$^c$ groups are taken together to represent an aromatic ring fused to the triazole ring, said aromatic ring being a member of the group consisting of phenyl, pyridine, pyrazine, pyrimidine, pyrrole, imidazole, thiophene, furan or thiazole.

10. A composition comprised of an antibacterial effective amount of a compound in accordance with claim 1 in combination with a pharmaceutically acceptable carder.

11. A method of treating a bacterial infection in a mammalian patient in need of such treatment, comprising administering to said mammal a compound in accordance with claim 1 in an amount effective to treat said bacterial infection.

* * * * *

UNITED STATES PATENT AND TRADEMARK OFFICE
CERTIFICATE OF CORRECTION

PATENT NO. : 5,350,746
DATED : September 27, 1994
INVENTOR(S) : Alan D. Adams and James V. Heck It is certified that error appears in the above-indentified patent and that said Letters Patent is hereby corrected as shown below:

In Claim 5, at column 79, line 10, between the words "tetrazole" and "attached", please delete the word [ting] and insert the word -- ring --.

In Claim 10, at column 80, line 33, please delete the last word in the sentence [carder], and insert the word -- carrier --.

Signed and Sealed this

Twentieth Day of December, 1994

Attest:

BRUCE LEHMAN

*Attesting Officer*  *Commissioner of Patents and Trademarks*